United States Patent
Atiyeh et al.

(10) Patent No.: US 10,640,792 B2
(45) Date of Patent: May 5, 2020

(54) FERMENTATION CONTROL FOR OPTIMIZATION OF SYNGAS UTILIZATION

(71) Applicant: THE BOARD OF REGENTS FOR OKLAHOMA SATE UNIVERSITY, Stillwater, OK (US)

(72) Inventors: Hasan K. Atiyeh, Stillwater, OK (US); John Randall Phillips, Middletown, DE (US); Raymond L. Huhnke, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 0 days.

(21) Appl. No.: 15/526,558

(22) PCT Filed: Nov. 13, 2015

(86) PCT No.: PCT/US2015/060720
§ 371 (c)(1),
(2) Date: May 12, 2017

(87) PCT Pub. No.: WO2016/077778
PCT Pub. Date: May 19, 2016

(65) Prior Publication Data
US 2017/0356012 A1    Dec. 14, 2017

Related U.S. Application Data

(60) Provisional application No. 62/079,387, filed on Nov. 13, 2014.

(51) Int. Cl.
*C12P 7/06* (2006.01)
*C12P 7/54* (2006.01)
*C12Q 3/00* (2006.01)

(52) U.S. Cl.
CPC .............. *C12P 7/065* (2013.01); *C12P 7/54* (2013.01); *C12Q 3/00* (2013.01); *Y02E 50/17* (2013.01)

(58) Field of Classification Search
CPC ... C12P 7/065; C12P 7/54; C12Q 3/00; Y02E 50/17
USPC ...................................... 435/252.7
See application file for complete search history.

(56) References Cited

U.S. PATENT DOCUMENTS

| | | |
|---|---|---|
| 2012/0122173 A1 | 5/2012 | Gaddy et al. |
| 2013/0005010 A1 | 1/2013 | Bell et al. |
| 2014/0113341 A1 | 4/2014 | Nitz et al. |

OTHER PUBLICATIONS

Daniell et al., Commercial Biomass Syngas Fermentation, Energies, 5 (2012) pp. 5372-5417.*
Munasinghe et al, "Biomass-Derived Syngas Fermentation into Biofuels: Opportunities and Challenges", Jan. 21, 2010, pp. 5013-5022, Publisher: Bioresource Technology 101, Published in: US.
PCT/US2015/060720—International Search Report and Written Opinion, dated Jan. 22, 2016, Inventor: Atiyeh, et al., Title: Fermentation Control for Optimization of Syngas Utilization.

* cited by examiner

*Primary Examiner* — Jennifer M. H. Tichy
(74) *Attorney, Agent, or Firm* — Crowe & Dunlevy; Terry L. Watt

(57) ABSTRACT

Controlling the gas inlet flow rate and energy input to a fermentation reactor to maximize conversion of syngas by maximizing uptake of hydrogen into a medium relative to carbon dioxide and carbon monoxide based on determined volumetric mass transfer coefficients for hydrogen, carbon monoxide, and carbon dioxide.

14 Claims, 10 Drawing Sheets

FERMENTATION CONTROL FOR OPTIMIZATION OF SYNGAS UTILIZATION

CROSS REFERENCE TO RELATED APPLICATION

This application claims the benefit of U.S. Provisional Application No. 62/079,387 filed Nov. 13, 2014, herein incorporated by reference in its entirety for all purposes.

STATEMENT REGARDING FEDERAL SPONSORED RESEARCH OR DEVELOPMENT

This invention was made with U.S. Government support under USDA/NIFA Grant No. 2009-34447-19951 and USDA/NIFA Grant No. 2010-34447-20772 awarded by the Department of Agriculture and under DOT Grant No. DTOS59-07-G-00053 awarded by the Department of Transportation. The Government has certain rights in this invention.

TECHNICAL FIELD

This disclosure relates to fermentation for the production of useful products in general and, more specifically to fermentation for utilization of syngas.

BACKGROUND

Conversion of syngas, which may contain a mixture of hydrogen, carbon monoxide, carbon dioxide and other gases, into useful chemicals and substances may be accomplished by fermentation of these gases by acetogenic bacteria. Pursuant to such a process, relative concentrations of these gases within the liquid medium should be carefully controlled and monitored to maximize production of the desired end products, such as ethanol.

What is needed is a system and method for addressing the above, and related issues.

SUMMARY

The invention of the present disclosure, in one aspect thereof, comprises a method of syngas fermentation including providing a continuously stirred tank reactor having a gas inlet, a gas outlet, and a variable speed agitator, providing a liquid medium inside the continuously stirred tank reactor, and providing an autotrophic acetogenic bacteria in the medium. The method includes initiating fermentation of a feed gas by supplying syngas comprising carbon monoxide and hydrogen gases via the gas inlet at a first gas flow rate while operating the agitator at a first speed and detecting a concentration of hydrogen and a concentration of carbon monoxide from the gas outlet. The method also includes continuing fermentation while operating the agitator at a second speed that is greater than the first speed when a decrease in concentration of hydrogen and a decrease in concentration of carbon monoxide is detected from the gas outlet.

In some embodiments, the method includes further increasing the agitator speed from the second speed. The method may include reducing the gas flow rate upon detecting an increase in concentration of hydrogen gas at the outlet.

The invention of the present disclosure, in another aspect thereof, comprises providing a fermentation reactor having a gas inlet and a gas outlet and an energy input, providing a liquid medium inside the continuously stirred tank reactor, providing an autotrophic acetogenic bacteria in the medium, and providing a syngas into the gas inlet at a controlled rate. The method includes determining a volumetric mass transfer coefficient for carbon monoxide in the liquid medium and determining a volumetric mass transfer coefficient for hydrogen in the liquid medium. The method includes determining a volumetric mass transfer coefficient for carbon dioxide in the liquid medium, and controlling the gas inlet flow rate and the energy input to maximize uptake of hydrogen into the medium relative to carbon dioxide and carbon monoxide based on the determined volumetric mass transfer coefficients for hydrogen, carbon monoxide, and carbon dioxide, respectively.

In some embodiments, the volumetric mass transfer coefficients are determined utilizing the equation:

$$-\frac{1}{V_L}\frac{dn_{GAS}}{dt} = \frac{\left(\frac{k_{L,GAS}\, a}{V_L}\right)}{H_{GAS}} \frac{(p_{GAS,i} - p^*_{GAS}) - (p_{GAS,o} - p^*_{GAS})}{\ln\left(\frac{(p_{GAS,i} - p^*_{GAS})}{(p_{GAS,o} - p^*_{GAS})}\right)}$$

where $k_L$ is a liquid film mass transfer coefficient, a is area of the gas liquid interface, $V_L$ is a liquid volume into which gas is transferred, H is Henry's Law constant for gas dn/dt is a molar rate of transfer of gas species, p is a partial pressure of gas, p* is a partial pressure of dissolved gas by Henry's Law, i denoting inlet and o denoting outlet and gas indicates corresponding to carbon dioxide, carbon monoxide, and hydrogen.

In some embodiments the autotrophic acetogenic bacteria is *Clostridium ragsdaleii, Clostridium acetobutylicum, Clostridium beijerinckii,* or *Clostridium ljungdahlii*. The fermentation reactor may be a continuously stirred tank reactor and the energy input may be an agitator. The fermentation reactor might also be a packed column contactor and the energy input comprise pumping the medium.

BRIEF DESCRIPTION OF THE DRAWINGS

These and further aspects of the invention are described in detail in the following examples and accompanying drawings.

DETAILED DESCRIPTION

Figure 1:
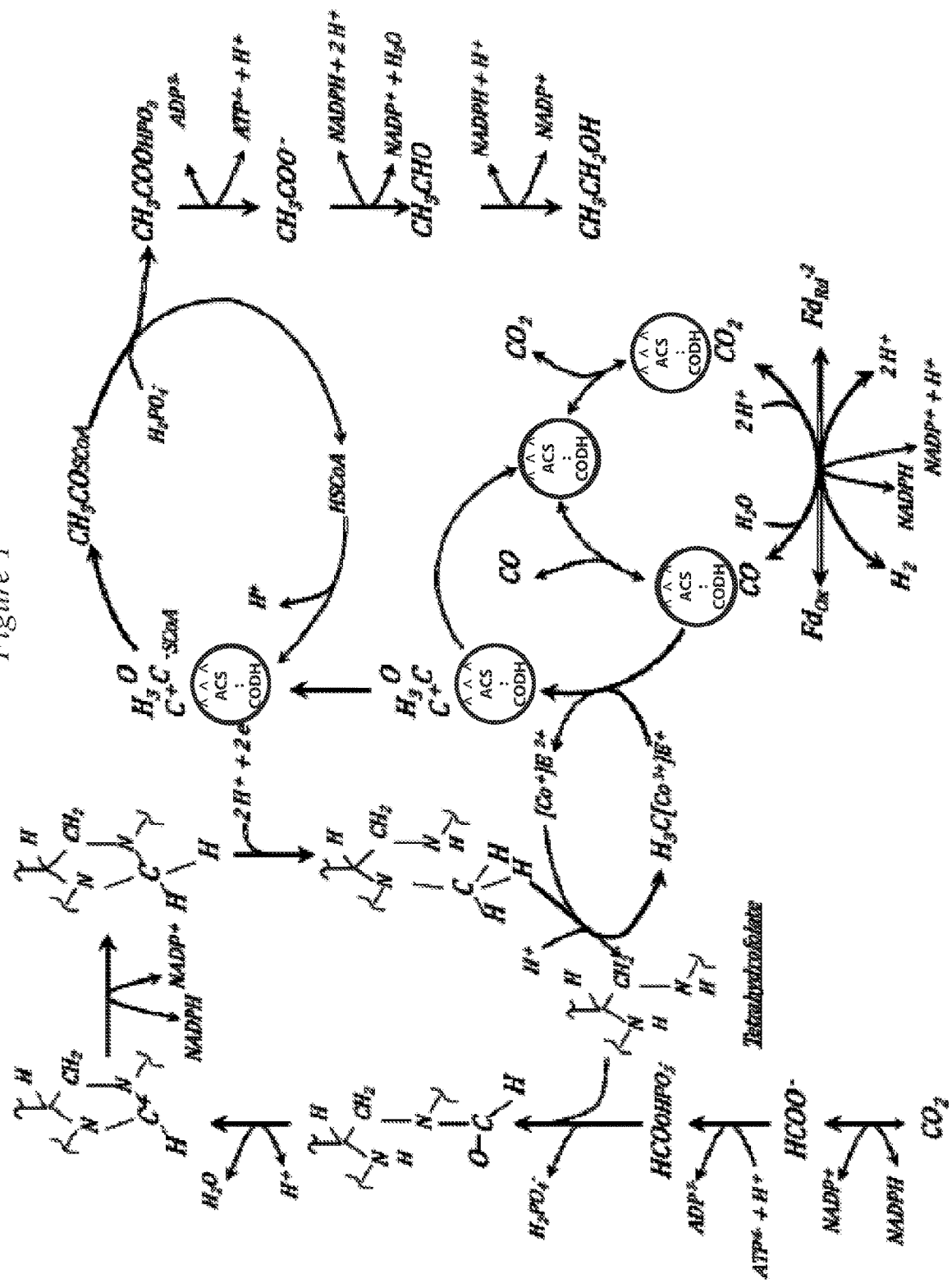
FIG. 1 illustrates the Wood-Ljungdahl or Acetyl-CoA pathway, after Phillips et al. (1994).

While this invention is susceptible of embodiment in many different forms, there is shown in the drawings, and will herein be described hereinafter in detail, some specific embodiments of the instant invention. It should be understood, however, that the present disclosure is to be considered an exemplification of the principles of the invention and is not intended to limit the invention to the specific embodiments or algorithms so described.

Autotrophic acetogenic bacteria, typically of the genus *Clostridium*, can convert CO and $H_2$ to acetic acid, ethanol and other useful industrial chemicals. CO and $H_2$ are the major components in gas produced by combustion of biomass and waste materials with less than stoichiometric $O_2$, often called synthesis gas, syngas or producer gas. Other sources of CO and $H_2$ are waste gases from steel production and similar processes. Acetogens derive energy and fix carbon from CO and $CO_2$ via a series of elementary reactions called the Wood-Ljungdahl or Acetyl-CoA pathway (Drake et al., 2008). The Wood-Ljungdahl pathway is depicted in FIG. 1, and includes an extension showing the reduction of acetic acid to ethanol (Phillips et al., 1994).

Products of syngas fermentation may include alcohols which are easily stored, transported and used in engines and chemical processes. Achieving high conservation of energy in the CO and $H_2$ requires high conversion of both CO and $H_2$ to recovered product. High specificity of product formed, in some embodiments, ethanol, maximizes yield. High concentration of the desired product enhances recovery. Productivity of a fermenter increases with high rates of gas consumption, and the rate of product formation is proportional. The optimized combination of these fermentation goals can minimize operating expense and maximize profitability of the process.

Systems and methods of the present disclosure may be employed with a variety of fermenters—both experimental and commercial or industrial in scale. In some embodiments, and in those provided herein by way of example, a continuously stirred tank reactor (CSTR), as is known in the art, may be employed. It will be appreciated that the various operational parameters as discussed herein should be controllable within the fermenter or fermentation process to take full advantage of the present disclosure. The disclosure is not limited to particular ways to implement the parameter control, rather one of skill in the art might conceive of numerous ways of providing adequate control within the bounds of the present disclosure.

The fermentation process is the in vivo solution of the mass transfer, stoichiometric, kinetic and thermodynamic parameters extant in the fermenter. CO and $H_2$ are sparingly soluble in the aqueous fermentation broth and must be continuously transferred into a broth or medium containing acetogenic single celled organisms (hereafter cells) to supply the cells for reaction. The capacity to absorb gas is defined by the mass transfer parameters. The cells have a limited capability to process absorbed gas; this capability is defined by the kinetic parameters exhibited by the culture in the chosen medium. Concentrations of the reactant gas species, CO, $H_2$ and $CO_2$, are thermodynamic quantities that determine the electrochemical potential or oxidation reduction potential (ORP) inside the cells. The ORP can affect proteins and metals in enzymes (Ragsdale, 2004), reduce the activity of the cells and lower the rate of conversion of CO and $H_2$ to ethanol product. The gas concentrations inside the cell are set by the rates of enzymatic reactions of the production pathway relative to the rates of gas supply. CO and $H_2$ transferred into the cell in excess of the kinetic capacity of the enzyme platform will accumulate up to saturation of the aqueous environment inside the cell. This accumulation of CO and $H_2$ at the enzymes in the cell determines the rate of the series of reactions, accumulation of intermediate metabolites, thermodynamic position of each distinct reaction and slate of products formed.

Design and control decisions for operating syngas fermentation may be determined considering a conceptual model of the fermentation process as discussed in the present disclosure. Mass transfer, stoichiometric, kinetic and thermodynamic correlations for the fermentation processes can be represented mathematically in a set of equations. These equations represent the conceptual model of fermentation derived from the known biochemical pathway and the structure of the cells, and can be used to build a computational model of the fermentation. Such a model as disclosed herein delivers an accurate assessment of fermentation conditions that may be suitable for design of equipment, and for incorporation in feedback control of gas supply and mass transfer (such as agitation speed in a stirred reactor) to maintain fermenter productivity at high conversions with high selectivity for the desired product.

Pathway

Autotrophic acetogens produce acetic acid from CO, $H_2$ and $CO_2$ via the Wood-Ljungdahl pathway (Phillips et al., 1994; Ragsdale, 2008) as shown in FIG. 1. CO and $CO_2$ provide carbon, while CO and $H_2$ provide energy in the form of electrons ($e^-$) and protons ($H^+$). A two-carbon compound, acetyl-CoA, is formed from $CO_2$ reduced to methyl, combined with CO and Coenzyme A. Acetyl-CoA is the source for all cell materials formed in the chemoautotrophic growth of the bacteria. Most of the acetyl-CoA is converted to acetic acid, recovering an ATP used to induce $CO_2$ into the reaction sequence. The primary purpose of the Wood-Ljungdahl pathway in acetogens is energy conservation for growth (Drake et al., 2008). Excess electrons can be used to reduce acetic acid through acetaldehyde to ethanol as a store of energy (Strobl et al., 1992; White et al., 1989). The reduction of acetic acid to ethanol is reversible, so that the acetogens can obtain energy for growth or maintenance from oxidation of ethanol to acetic acid (Adams, 2010). The reduction of acetic acid to ethanol represents a redox couple that can be exploited for energy storage and acts as a redox buffer.

Thermodynamics

The Wood-Ljungdahl pathway is an ordered set of chemical reactions occurring in sequence to produce acetyl-CoA, acetic acid and ethanol from $CO_2$, CO and $H_2$. Each reaction is mediated by an enzyme that catalyzes the reaction and proceeds in the direction of favored thermodynamics, for which the Gibbs free energy change ($\Delta G$) is less than zero. Thermodynamics of biological reactions are addressed in biochemistry texts (Lehninger, 1982; Nicholls and Ferguson, 2002); these treatments state the criteria for a reaction to proceed, $\Delta G<0$, and for thermodynamic equilibrium, $\Delta G=0$, and the dependence of $\Delta G$ on concentration of reactants and products through the mass action ratio (Nicholls and Ferguson, 2002). The effect of pH on $\Delta G$ is not discussed extensively, although Lehninger (1982) notes, "Biochemical reactions take place near pH 7.0 and often involve $H^+$," to introduce the standard free energy at pH 7.0, $\Delta G^{0'}$. The dependence of $\Delta G$ on pH and the application in redox reactions in the cell are discussed in Cramer and Knaff (1991). Cramer and Knaff (1991) emphasize the division of the intracellular space where the enzymes reside from the bulk liquid in fermentation. Measurements like pH and oxidation-reduction potential (ORP) are taken in the bulk liquid rather than inside the cell. Thermodynamic data for reactions and compounds of interest in biological systems are available in the appendix of Thauer et al. (1977), and this data can be used to define the thermodynamic position of the reactions of the Wood-Ljungdahl pathway.

Boghigian et al. (2010) used a computer algorithm to identify feasible pathways directed to chosen fermentation products as a guide for genetic design of *Escherichia coli*. The algorithm uses a group contribution method to compute the Gibbs free energy of formation ($\Delta G_f^o$) for intermediate metabolites, assess thermodynamic feasibility of the pathway from the overall free energy change and identify strongly unfavorable individual reactions. The method can be used to select pathways favoring growth or product formation.

A review of modeling techniques used to identify feasible pathways for genetic design is given by Medema et al. (2012). Many of these models use thermodynamic analysis and assembly of individual reactions forming a pathway to suggest plausible sequences from substrate to product.

Group contribution methods are also used to assess thermodynamics from free energy of formation in Henry et al. (2007), and the thermodynamic potential from reactions at pH 7.0 are used to define the range of concentrations of intermediate metabolites that support mass flux through identified pathways. Generally these models are designed to loosely define potentially feasible paths from substrate converted to products and identify particular reactions that can be down regulated by genetic modification. Thermodynamics have been examined for syngas fermentation (Hu et al., 2011) using transformed thermodynamics, and it was concluded that CO was always preferred over $H_2$ as a substrate for fermentation. CO inhibition of hydrogenase or thermodynamic disfavor was suggested as reason for low and delayed uptake of $H_2$ in syngas fermentation. These thermodynamic calculations assumed bulk liquid concentration saturated from the gas phase partial pressures of $H_2$, CO and $CO_2$. Acetogenic fermentation of gas containing both CO and $H_2$ can exhibit periods of exclusive CO uptake, but typically, CO and $H_2$ are consumed together (Phillips et al., 1993).

Mass Transfer

CO and $H_2$ are absorbed into liquid fermentation medium and into the cells by gas to liquid mass transfer. Mass transfer has been studied for syngas in various fermenters (Klasson et al., 1992; Munasinghe and Khanal, 2010; Vega et al., 1989) with the purpose of providing more mass transfer to achieve higher productivity. However, a transition from a kinetic limit, to a mass transfer limit, and return to kinetic limitation was shown for fermentation in batch bottles for which mass transfer capacity is expected to be constant (Phillips et al., 2011).

Vega et al. (1989) modeled mass transfer of CO into fermentation using *Peptostreptococcus productus* to produce acetate and estimated CO conversion and uptake as a function of feed gas flow and $k_{L,CO}a/V_L$. In the model, mixed flow of the gas phase using the effluent composition to define $k_{L,CO}a/V_L$ was assumed. This makes $k_{L,CO}a/V_L$ independent of gas flow, so $k_{L,CO}a/V_L$ changes only with agitation. This model was linked to the kinetic capability of a generic culture to consume a single substrate through a Monod model for CO as substrate (Klasson et al., 1992). It was asserted that the mass transfer will match the kinetic rate in either mass transfer limitation or under kinetic limitation. Klasson et al. (1992a) stated that optimum design and operation will balance the rate of substrate supply and the capacity of the culture to convert the delivered gas.

Mass transfer in a continuously stirred tank reactor (CSTR) is addressed by Bakker et al. (1994) and prediction of $k_{L,CO}a/V_L$, into water is based on the geometry of the fermenter, the power input and the gas flow through the liquid. The general method is useful in that mass transfer can be scaled approximately for similar geometry in the CSTR, and the form matches correlations reviewed in Garcia-Ochoa and Gomez (2009), as in Equation 1.

$$\left(\frac{k_{L,CO}\,a}{V_L}\right)_2 = \left(\frac{k_{L,CO}\,a}{V_L}\right)_1 \left(\frac{N_2}{N_1}\right)^\alpha \left(\frac{G_2}{G_1}\right)^\beta \quad (1)$$

Where N is the agitation speed (rpm), and G is the gas flow (ml/min, actual), and states 1 and 2 represent different conditions of agitation and gas flow. The exponents are reported to range from 0.5 to 3 for $\alpha$ with typical value of 1.8, and $\beta$0.3 to 0.8 for with a typical value of 0.6 (Garcia-Ochoa and Gomez, 2009). The correlation by Bakker et al. (1994) implies that the appropriate model for gas flow in the CSTR is plug flow, wherein fresh gas enters the liquid volume and the concentration of substrate gas is depleted before the bubble of spent gas leaves the liquid. The mass transfer is defined by the agitation and the volumetric gas flow rate through the liquid. The mass transfer model must appropriately represent the contact of gas and liquid in the fermenter under consideration.

Fermentation Control

The production of reduced products in the acetone-butanol-ethanol fermentation is affected by nutrient limitation of *Clostridium acetobutylicum* or *C. beijerinckii*, particularly limitation of nitrogen or phosphate (Rogers, 2006). This is described as an acidogenic growth phase that produces acetic and butyric acids, followed by a solventogenic stationary phase in which solvents are produced and the acids are consumed.

The expectation of acidogenesis followed by stationary phase solventogenesis has been popular in describing production of ethanol from synthesis gas by C. ljungdahlii and other related species (Kundiyana et al., 2011; Liu et al., 2012; Maddipati et al., 2011; Ramachandriya et al., 2010; Tracy et al., 2012). The shift to ethanol production was induced by omission of yeast extract and accompanied slower growth in the defined medium to achieve concentrations of more than 20 g/L in continuous culture (Phillips et al., 1993). The manipulation of medium composition to establish metabolic control is the basis of development to commercial production of ethanol via synthesis gas fermentation (Gaddy, 2007). This control is grounded in the reactions of the Wood-Ljungdahl pathway (Phillips et al., 1994) and distributes electrons derived from CO and $H_2$ toward formation of the reduced product ethanol. The basis of this distribution and control of fermentation is, as yet, poorly defined.

Integration of the conceptual model of syngas fermentation, thermodynamic and mass transfer analyses, and metabolic control derived from the biological pathway in an overall description of the fermentation process will enhance the analysis and process performance, allow more effective planning of experiments and provide a vehicle for feedback of the knowledge derived to provide a more perfect model of the syngas fermentation.

The present disclosure provides, among other information, mathematical equations for mass balance, mass transfer and thermodynamics that form a foundation of a computer model of syngas fermentation. The calculations can be applied in syngas fermentations and model predictions compared with experimental results.

Conceptual Model Development

A mathematical model can be used to analyze fermentation data or to predict the performance of planned fermentation. Analysis uses input from measurements of performance and derived parameter values to develop correlations of culture performance. Predictions are made with assumed input data to specify fermentation performance. Typical input data to the model includes the rate and composition of feed gas, and required or observed conversion of CO and $H_2$, production of $CO_2$, ethanol and acetic acid.

Figure 2:
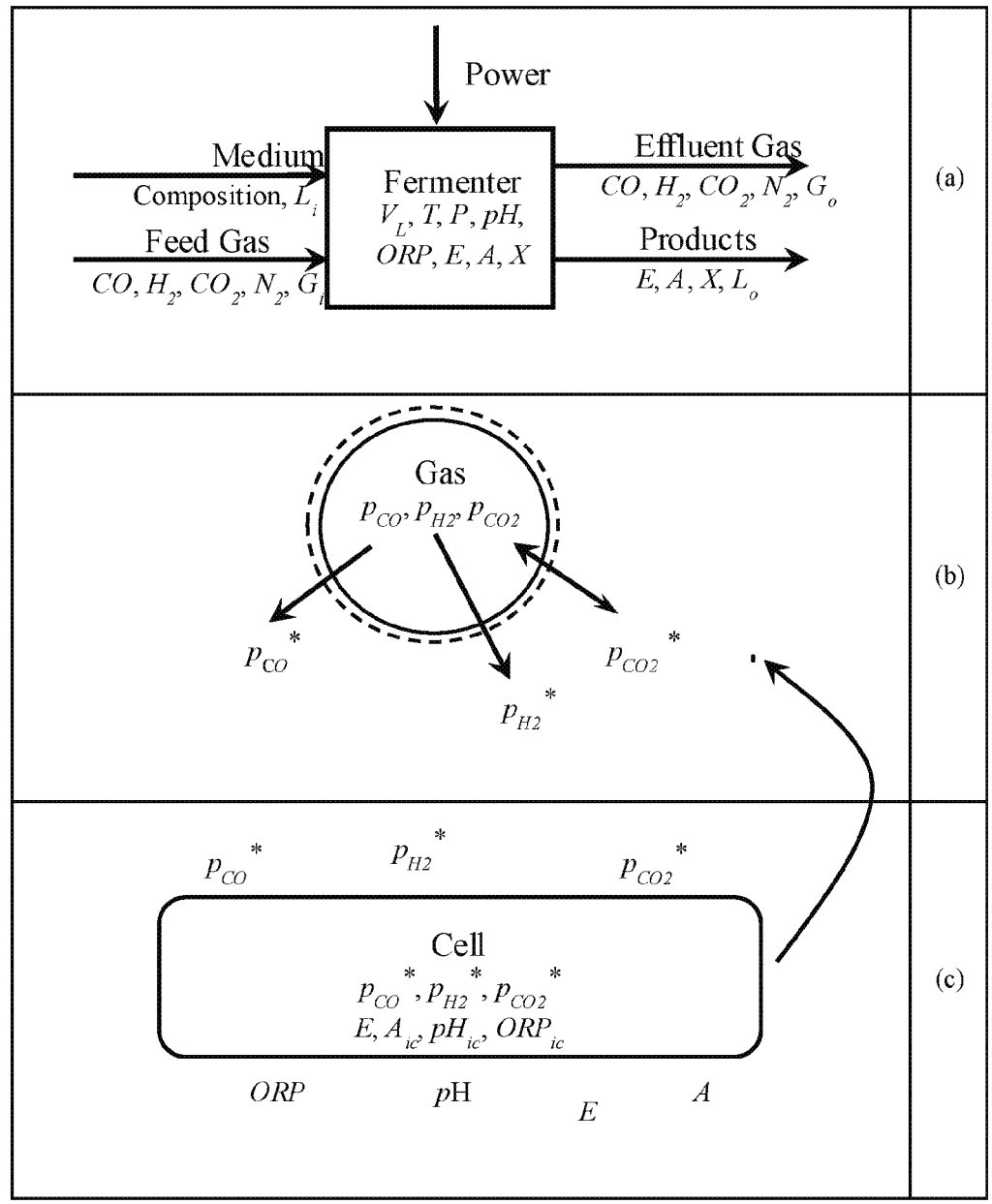
FIG. 2 illustrates a scale of fermentation according to the present disclosure: (a) Macroscopic level, measurable parameters and controlled inputs. (b) Intermediate level, mass transfer. (c) Microscopic level, in the bulk liquid and inside the cell, separated by the cell membrane. Liquid flow (L) in ($L_i$) and out ($L_o$), gas flow (G), gas composition (mole fraction CO, $H_2$, $CO_2$, $N_2$), fermenter liquid volume ($V_L$), temperature (T), pressure (P), pH, oxidation reduction potential (ORP), liquid concentrations (g/L ethanol (E), acetic acid (A), cells (X)), gas phase partial pressure pCO, $pH_2$, $pCO_2$ (kPa), bulk liquid phase gas concentration as partial pressure pCO*, $pH_2$*, $pCO_2$* (kPa), intracellular $pH_{ic}$.

The conceptual fermentation model is based on conversion of CO and $H_2$ to acetic acid and ethanol that is effected at a molecular scale inside the cells. However, measurements are taken (these according to methods known in the art) and control functions are exercised at the macroscopic scale of the fermenter. Macroscopic, intermediate and microscopic conceptual views of the fermentation are depicted in FIG. 2, showing the parameters that are effective within each view. Equipment and methods, such as agitation speed in a CSTR, packing design in column reactors, and control of pH, flows, and pressures must be used at the macroscopic level to direct the reactions that occur in the microscopic scale. The conceptual and mathematical models of the fermentation according to the present disclosure must relate the control actions to the biochemical reactions inside the cell where the results are determined.

Macroscopic Scale

Measurements and control parameters are generally available at the macroscopic level of the fermentation. The flows and compositions of the inlet and effluent streams are known and determined to achieve targeted rates of product formation and conversion of CO and $H_2$. The medium provides the components for assembly of the platform of enzymes. Minerals and metals that set the active sites of enzymes and cofactors, and essential vitamins that are not synthesized by the culture are provided in this nutrient stream. The design of the nutrient medium affords control of the operating concentration of cells, denoted as X in FIG. 2. Cell retention can increase the concentration of cells in the fermenter; however, to be productive, the cells must retain activity in conversion of CO and $H_2$ to ethanol. Carbon and hydrogen in the carbohydrate and protein structure of the cells that contain the enzymes are taken from CO and $H_2$ in the feed gas. The CO and $H_2$ contain the energy that is to be captured in the ethanol product. The effluent gas is the residue of the feed gas. The difference in CO and $H_2$ content of the inlet and effluent gas streams reflects the conservation of energy to products. The liquid product stream contains the output of the fermentation, the preferred product is ethanol that can be recovered.

Wastes that must be processed include a purge of cells, acetate buffer and unrecovered ethanol that are discarded in wastewater. The fermenter system contains the liquid volume, retains the inventory of active cells, receives CO and $H_2$ absorbed from the gas, and accumulates liquid products, ethanol and acetic acid. Physical parameters that define the fermentation like pH, temperature, pressure and ORP are measured and controlled in the macroscopic environment (FIG. 2a).

Mass transfer moves CO and $H_2$ into the liquid volume to supply reactions, and is effected by macroscopic design and control. Mass transfer is promoted by applied power in the form of agitation for gas dispersion in the CSTR or pumping of the liquid in packed column contactors, and gas compression for sparging or membrane transfer. These implements may be referred to an input power to a fermentation reactor or system. Assessment of performance from rates of change of gas and product compositions, and control of parameters affecting the fermenter performance are conducted at the macroscopic scale of the fermentation.

Intermediate Scale

Mass transfer of CO, $H_2$ and $CO_2$ in the intermediate view of fermentation provides a bridge between the macroscopic environment of observation and control, and the molecular environment of reaction in FIG. 2b. CO and $H_2$ are absorbed and $CO_2$ is removed through a stagnant liquid film between the gas and the well mixed bulk liquid. Transfer of CO or $H_2$ is driven by concentration difference across this film at a rate that matches the consumption in the cells. CO and $H_2$ accumulate in the bulk liquid to a concentration that supports the rate of reaction inside the cells, and the rate of transfer slows to match the reaction rate. Accumulated CO and $H_2$ can slow fermentation reactions through inhibition of crucial enzymes. The balanced rates of mass transfer and reaction set the dissolved concentrations of the gases and determine the products that are formed.

Microscopic Scale

Conversion of CO and $H_2$ to acetic acid, ethanol and celass is conducted on a platform of enzymes contained in the cells (FIG. 2c). The cell membrane separates the cytoplasm from the bulk liquid fermentation broth, and the enzymes are either suspended in the cytoplasm or associated with or embedded in the membrane. Intracellular conditions of pH, ORP, and chemical composition are related to the bulk liquid by diffusion and membrane transport, and can differ in significant ways that are essential to cell function (Cramer and Knaff, 1990; Nicholls and Ferguson, 2002). The concentrations of dissolved CO, $H_2$ and $CO_2$ inside the cells are nearly the same (within 5% difference) as the bulk liquid, since transfer of gas into the cells occurs along a short mass transfer path through a very thin membrane (6 to 9 nm thick) with a large total surface area. The observed rates of consumption of gas and formation of products in the defined stoichiometry of the production pathway reveal the mass flux of carbon, protons and electrons through the pathway reactions. The dissolved gas concentrations set the thermodynamics of reactions, determine the kinetic rates, and also set the concentrations of intermediate metabolites. The fermentation happens in this intracellular environment, and the mass flux through the biological pathways can be quantified and controlled to achieve targeted results on the macroscopic scale as shown by the present disclosure.

Mathematical Model Development

Mass Transfer and Dissolved Gas Concentrations

Since the fermentation reactions occur inside the cell, and rates and thermodynamics are dependent on the concentrations of reactants, starting with CO and $H_2$, the intracellular conditions must be determined for use in model calculations. The first step in the model development is to define the capacity for mass transfer of CO, $H_2$, and $CO_2$, and estimate the concentrations of these gas species in bulk liquid and in the cell.

CO and $H_2$ are sparingly soluble in water and their solubility depends on the partial pressure of the individual species according to Henry's Law. For CO, as an example.

$$C_{CO} = y_{co} P_T / H_{CO} \quad (2)$$

Where $C_{CO}$ is the liquid phase concentration of CO, $y_{co}$ is the gas phase mol fraction of CO, $P_T$ is the total pressure and $H_{CO}$ is the Henry's Law constant for CO. The Henry's Law constants for CO, $H_2$ and $CO_2$ at 37° C. are given in Table 1. Saturated concentration of either CO or $H_2$ in water under 100 kPa of pure gas will be less than $10^{-3}$ mol/L. CO and $H_2$ must be continuously replenished in the liquid medium to support active fermentation. The lowest concentrations of CO and $H_2$ are inside the cell where the enzymes that catalyze oxidation reside. $CO_2$, in contrast, is produced in fermentation that consumes CO. $CO_2$ is transferred from inside the cell through the liquid phase to the gas phase. The concentration of $CO_2$ will be highest inside the cell.

TABLE 1

Henry's Law constants and diffusivities for gases in water at 37° C.[a]

| Gas | H (kPa L/mol) | $D_{i,w}$ ($m^2$/s) |
| --- | --- | --- |
| CO | 121561 | $2.50 \times 10^{-9}$ |
| $H_2$ | 140262 | $6.24 \times 10^{-9}$ |
| $CO_2$ | 4240 | $2.69 \times 10^{-9}$ |
| $O_2$ | 101300 | $3.25 \times 10^{-9}$ |

[a]After (Hougen et al., 1954)

The rate of mass transfer of substrate gas from the bulk gas through the gas-liquid interface and the bulk liquid into the cell can be described by film theory (Bird et al., 2002). Diffusion of gas components within the bulk gas is very fast relative to the consumption rate and the concentration of each species is uniform throughout the gas phase. The concentration of each species in the liquid at the interface is at equilibrium with the bulk gas partial pressure as predicted by Henry's Law (Equation 2). The liquid at the interface is part of a stagnant film of fluid through which dissolved gas must transfer by diffusion to the bulk liquid. Diffusion is driven by concentration difference and is dependent on the gas diffusivity through water and the thickness of the stagnant film. Outside the liquid film, the liquid is assumed to be mobile and turbulent (Charpentier, 1981), and gas transfer within the bulk liquid is by bulk flow at rates far exceeding diffusion. The bulk liquid is assumed to be well mixed and homogeneous. Gas is transferred into the cell by a diffusion process through the cell membrane, which is 6 to 9 nm thick. *C. ragsdalei* cells are typically 0.5 μm diameter by 3 μm, and even at low cell density (0.02 g cells/L), there are more than $10^{1°}$ cells/L of bulk liquid. The surface area of these cells will exceed the area of the gas-liquid interface by 2 to 3 orders of magnitude in a typical fermentation. Gas-to-liquid mass transfer rate is controlled by diffusion through the film of stagnant liquid at the gas-liquid interface. The rate of molar gas transfer is proportional to the difference in concentration from the surface of the liquid to the bulk liquid.

The partial pressure of each component in the gas phase is the product of its mole fraction and the total pressure, for CO $$p_{co} = y_{co} P_T \quad (3)$$

And the liquid film mass transfer is represented by Equation 4.

$$-\frac{1}{V_L}\frac{dn_{CO}}{dt} = \frac{k_{L,CO} a}{V_L}(c^*_{CO} - c_{CO,L}) = \frac{\left(\frac{k_{L,CO} a}{V_L}\right)}{H_{CO}}(p_{CO} - p^*_{CO}) \quad (4)$$

Where $c_{CO}^*$ is concentration of CO at the interface surface in equilibrium by Henry's Law and $c_{CO,L}$ is concentration in the bulk liquid, $p_{CO}^*$ is the CO partial pressure (kPa) in equilibrium by Henry's Law with the concentration of CO dissolved in the bulk liquid and $p_{CO}$ is partial pressure in the gas bubble, $H_{CO}$ is the Henry's Law constant for CO (kPa L/mol) and $V_L$ is the volume (L) of liquid into which gas is transferred. The molar rate of transfer is $-dn_{CO}/dt$ (mol CO/h) where the negative sign denotes consumption from $n_{CO}$ moles of CO in the bulk gas. The constant of proportionality is ($k_{L,CO}$ $a/V_L$) and is the overall liquid film mass transfer coefficient for CO with units of reciprocal time ($h^{-1}$). a is the area ($m^2$) of the gas/liquid interface. The term $k_{L,CO}$ is the liquid film mass transfer coefficient for CO (L/$m^2$ h). $k_{L,CO}$ includes effects of turbulence in the liquid, hydrodynamic conditions like viscosity that affect film thickness, and the effect of diffusivity in the aqueous phase.

In a CSTR, fresh gas enters as a bubble and is suspended in the liquid while CO and $H_2$ are removed by mass transfer to the cells. The bubble depleted of CO and $H_2$ leaves the liquid into the headspace of the fermenter. The difference of CO concentration between the bubble surface and the bulk liquid falls as CO is consumed from the gas bubble. Overall in the CSTR, the effective concentration difference is best represented with a plug flow model and calculated as the logarithmic mean of the concentration difference between the inlet gas and the bulk liquid, and the concentration difference between the effluent gas and the bulk liquid.

$$-\frac{1}{V_L}\frac{dn_{CO}}{dt} = \frac{\left(\frac{k_{L,CO}a}{V_L}\right)}{H_{CO}}\frac{(p_{CO,i}-p_{CO}^*)-(p_{CO,o}-p_{CO}^*)}{\ln\frac{(p_{CO,i}-p_{CO}^*)}{(p_{CO,o}-p_{CO}^*)}} \quad (5)$$

Similar equations can be written to describe mass transfer for $H_2$ and $CO_2$.

When the diffusion of CO through the liquid film is slow the concentration of CO in the bulk liquid is depleted by reaction. The concentration difference across the liquid film is at a maximum, and the overall process of gas consumption is mass transfer limited. The concentration of CO in the bulk liquid approaches zero and $$p^*_{CO} \approx 0 \quad (6)$$

CO inhibits the enzyme hydrogenase severely at dissolved pressures greater than about $2\times10^{-3}$ kPa, and 50% inhibition is reported at $8.5\times10^{-4}$ kPa (Ragsdale and Ljungdahl, 1984). Since $2\times10^{-3}$ kPa is negligible when subtracted from the 1 kPa of CO measured in residual syngas at high conversion, the uptake of $H_2$ is a sensitive indicator that CO is mass transfer limited. In the case where $H_2$ and CO are converted simultaneously, CO mass transfer can be calculated, with confidence, assuming zero concentration in the bulk liquid. The mass transfer capability for CO can be quantified as $k_{L,CO}a/V_L$. The mass transfer in the CSTR is calculated according to Equation 5, which is solved for $k_{L,CO}a/V_L$ with $p_{CO}^*=0$ to obtain Equation 7.

$$\left(\frac{k_{L,CO}a}{V_L}\right) = -\frac{H_{CO}}{V_L}\frac{dn_{CO}}{dt}\frac{\ln\left(\frac{p_{CO,i}}{p_{CO,o}}\right)}{p_{CO,i}-p_{CO,o}} \quad (7)$$

Where $p_{CO,i}$ is the partial pressure of CO in the inlet gas and $p_{CO,o}$ is the CO partial pressure in the effluent gas. The interfacial area per liquid volume, $a/V_L$, is the same for the different gas species, and $k_{L,H2}$, $k_{L,CO}$ and $k_{L,CO2}$ differ only by the ratio of the square root of their diffusivities in water. Values of $k_{L,H2}a/V_L$ and $k_{L,CO2}a/V_L$ can be predicted from $k_{L,CO2}a/V_L$ with confidence using Equation 8.

$$\frac{k_{L,CO}a}{V_L} = \sqrt{\frac{D_{CO,W}}{D_{H2,W}}}\left(\frac{k_{L,H2}a}{V_L}\right) = \sqrt{\frac{D_{CO,W}}{D_{CO2,W}}}\left(\frac{k_{L,CO2}a}{V_L}\right) \quad (8)$$

Where $D_{CO,W}$, $D_{H2,W}$ and $D_{CO2,W}$ are the diffusivities of CO, $H_2$ and $CO_2$ in water at fermentation temperature, typically 37° C. as given in Table 1.

The partial pressures of dissolved $H_2$ and $CO_2$, $p_{H2}^*$ and $p_{CO2}^*$, can be determined from the gas phase partial pressure, the uptake of $H_2$ and $CO_2$ and $k_{L,CO}a/V_L$ obtained for mass transfer limited CO. The value of $k_{L,CO}a/V_L$ is found from Equation 7, which assumes $P_{CO}^*=0$. Using $D_{CO,W}$, $D_{H2,W}$, and $D_{CO2,W}$ to find $k_{L,H2}a/V_L$ and $k_{L,CO2}a/V_L$, Equation 5 can be written for $H_2$ and solved explicitly for $p_{H2}^*$ as in Equation 9; and again writing Equation 5 for $CO_2$, the explicit solution for $pCO_2^*$ is Equation 10. No assumption of mass transfer limitation is made for $H_2$, or $CO_2$ in Equations 9 and 10; however, CO is assumed limited to define the mass transfer coefficients from the experimental data.

$$p_{H2}^* = \frac{\left(p_{H2,i} - p_{H2,o}\exp\left[\frac{\left(\frac{k_{L,H2}a}{V_L}\right)}{H_{H2}}\frac{(p_{H2,i}-p_{H2,o})}{\left(-\frac{1}{V_L}\frac{dn_{H2}}{dt}\right)}\right]\right)}{\left(1-\exp\left[\frac{\left(\frac{k_{L,H2}a}{V_L}\right)}{H_{H2}}\frac{(p_{H2,i}-p_{H2,o})}{\left(-\frac{1}{V_L}\frac{dn_{H2}}{dt}\right)}\right]\right)} \quad (9)$$

$$p_{CO2}^* = \frac{\left(p_{CO2,i} - p_{CO2,o}\exp\left[\frac{\left(\frac{k_{L,CO2}a}{V_L}\right)}{H_{CO2}}\frac{(p_{CO2,i}-p_{CO2,o})}{\left(-\frac{1}{V_L}\frac{dn_{CO2}}{dt}\right)}\right]\right)}{\left(1-\exp\left[\frac{\left(\frac{k_{L,CO2}a}{V_L}\right)}{H_{CO2}}\frac{(p_{CO2,i}-p_{CO2,o})}{\left(-\frac{1}{V_L}\frac{dn_{CO2}}{dt}\right)}\right]\right)} \quad (10)$$

The parameters in Equations 9 and 10 are as defined above for CO, with $dn_{H2}/dt$ and $dn_{CO2}/dt$ being the uptake rates of $H_2$ and $CO_2$ from the experimental data.

Water gas shift reaction and $p_{CO}^*$

CO and $H_2$ are typically consumed simultaneously and electrons pass from both hydrogenase and CO dehydrogenase to ferredoxin and are distributed to other carriers inside the cell. Electron flow is toward ferredoxin from CO and $H_2$, and the water gas shift reaction (Equation 11) that relates concentrations of CO, $H_2$ and $CO_2$ is in thermodynamic equilibrium inside the cell.

$$CO + H_2O \leftrightarrow CO_2 + H_2 \quad (11)$$

The Gibbs free energy change for the water gas shift reaction can be calculated as in Equation 12 with $\Delta G_r = 0$, and for the reaction in Equation 11, $\Delta G_r^O = -19.93$ kJ/mol, which was calculated using $\Delta G_f^O$ from Thauer et al. (1977).

$$\Delta G_r = \Delta G_r^o + RT\ln\left(\frac{p_{CO2}^* p_{H2}^*}{p_{CO}^*}\right) = 0 \quad (12)$$

The equilibrium mass action ratio (Nicholls and Ferguson, 2002) for the water gas shift reaction can be calculated from Equation 12, and $p_{CO}^*$ can be calculated with $p_{H2}^*$ and $p_{CO2}^*$ from Equations 9 and 10. The units in Equation 13 are converted, from the standard state of 1 atm $H_2$, to kPa (101.3 kPa/atm) and for 37° C.

$$\frac{p_{CO2}^* p_{H2}^*}{p_{CO}^*} = e^{\left(\frac{-\Delta G_r^o}{RT}\right)} = 101.3e^{\left(\frac{-(-19.93)}{(0.008314)(310.2)}\right)} = 230,100 \, kPa \quad (13)$$

The calculated value of $p_{CO}^*$, less than $10^{-2}$ kPa, can be used to check the validity of the assumption of CO mass transfer limitation (i.e., $p_{CO}^* \approx 0$).

This estimation of dissolved gas pressures is only valid when both CO and $H_2$ are consumed. Hydrogenase is 50% inhibited by $7\times10^{-9}$ mol/L CO ($p_{CO}^* = 8.5\times10^{-4}$ kPa) (Ragsdale and Ljungdahl, 1984), and there are large potential errors (orders of magnitude) in the calculation of $p_{CO}^*$ since activity of hydrogenase will be diminished until CO concentration in the cell is less than $7\times10^{-9}$ mol/L. Since accumulated CO will inhibit hydrogenase and slow the oxidation of $H_2$, the effective pressure of $H_2$ seen by ferredoxin will be lower (10% or less) than the estimated partial pressure of $H_2$ delivered to the hydrogenase. Since the calculated $p_{CO}*$ is proportional to $p_{H2}*$, the dissolved pressures calculated from Equations 9 through 13 can be higher than $p_{CO}*$ and $p_{H2}*$ operating to reduce ferredoxin in the cell reactions. However, $p_{CO}*$ and $p_{H2}*$ calculated from Equations 9 through 13 are useful as the best available approximation of the thermodynamic condition inside the cell, and are reasonable parameters to characterize reaction kinetics.

Electrochemistry

Many reactions in the Wood-Ljungdahl pathway are oxidation-reduction reactions, in which electrons are transferred from one molecule to another; the electron donor is oxidized, and the electron acceptor is reduced. The water gas shift reaction in Equation 11 provides an example; CO is oxidized to $CO_2$ and $H^+$ is reduced to $H_2$. This can be understood as oxidation of CO coupled with reduction of $H^+$ by writing the half-reactions for CO oxidation, Equation 14, $$CO + H_2O \leftrightarrow CO_2 + 2H^+ + 2e^- \quad (14)$$

and for $H^+$ reduction, Equation 15.

$$2H^+ + 2e^- \leftrightarrow H_2 \quad (15)$$

These half-reactions sum to the overall water gas shift reaction (Equation 11), and CO is shown to donate two $e^-$ to produce $H_2$. This reaction is reversible, and $H_2$ can be oxidized to produce CO from $CO_2$. Reaction will proceed in the direction for which $\Delta G_r < 0$. The reaction will be in equilibrium when $\Delta G_r = 0$.

The reduced and oxidized forms of a chemical comprise a redox couple, for example $H_2/H^+$ and $CO/CO_2$. The oxidized form will accept electrons (and sometimes $H^+$) to become the reduced form. When the half-reaction is set at the standard condition of 1.0 mol/L reactants and products, the redox couple will exhibit a characteristic tendency or potential to donate electrons. This potential, measured in volts, with equal concentrations of the oxidized and reduced forms, is the midpoint potential. This is $E^0$ at pH 0. $E^0$ for a half-cell reaction can be calculated from $\Delta G_r^0$ as in Equation 16 (Nicholls and Ferguson, 2002; Thauer et al., 1977).

$$E^0 = -\Delta G_r^0 / n_e F \quad (16)$$

Where $n_e$ is the number of electrons transferred and F (0.0965 kJ/mV mol $e^-$) is the Faraday constant. Note that this potential is a characteristic of the half-cell reaction, not a differential. The Gibbs free energy change for a half-cell reaction, $\Delta G_r$, changes with concentrations of products and reactants. The electrochemical potential of the half-cell also changes. The potential (E) is given by the Nernst Equation (Bailey and Ollis, 1986; Nicholls and Ferguson, 2002).

$$E = -\frac{\Delta G_r}{n_e F} = \quad (17)$$

$$E^o - \frac{RT}{n_e F} \ln\left(\prod C_{(Products)} / \prod C_{(Reactants)}\right) + 2.302 \frac{RT}{n_e F} \Delta m_H pH$$

The notation ($\Pi C_{products}/\Pi C_{Reactants}$) represents the mass action ratio for the reaction (Nicholls and Ferguson, 2002), and $\Delta m_H$ is the number of protons produced in the reaction. E is the potential of the redox couple to donate electrons under the actual conditions, and each redox couple will exhibit its characteristic potential under those conditions. A redox couple with lower (more negative) potential will donate electrons (be oxidized) to couples of higher potential.

Two half-cell reactions are combined, an oxidation with a reduction, in a balanced reaction, as shown above for the water gas shift reaction where Equations 14 and 15 are combined in Equation 11. When the reaction reaches equilibrium, $\Delta G_r = 0$ and both redox couples are at the same potential E (or $\Delta E_r = 0$).

When mass transfer is rate limiting, the transfer of gas to the cell is the slowest process in the fermentation, and all reaction steps in the production pathway are fast relative to the rate of gas supply. Under mass transfer limitation, the reactions of the production pathway approach thermodynamic equilibrium, and all electrochemical half-cell reactions inside the cell are set at the same potential, $E_{Cell}$. The assumption of thermodynamic equilibrium at one intracellular potential sets a boundary condition that defines the thermodynamic state of the pathway reactions. The approach of the reactions to this ideal thermodynamic state provides a reasonable and convenient method to describe the reaction set for study and modeling of syngas fermentation.

The potential of the oxidation reduction reactions of the pathway can be estimated by Equation 17 with $E^0$ calculated from Equation 16. Then Equation 17 can be rearranged to calculate the mass action ratio as in Equation 18.

$$\left(\prod C_{(Products)} / \prod C_{(Reactants)}\right) = \quad (18)$$

$$\exp\left[-\frac{\Delta G_r^o}{RT} - \frac{n_e FE}{RT} + 2.302 \Delta m_H pH\right]$$

Ratios of products for selected half-cell reactions from the Wood-Ljungdahl pathway are presented in Table 2. Note that the ratios of products to reactants are ratios of concentrations or partial pressures, except for the partial pressure of $H_2$. The half-cells are typically two electron reductions, $n_e = 2$, and that most reductions consume two protons, $\Delta m_H = -2$, except NADH/NAD$^+$ and $Fd_r/Fd_o$ consume one proton and no protons respectively. The values of $\Delta G^{0\prime}$ and $E^{0\prime}$ are calculated at pH 7.0 and match values given by Thauer et al. (1977).

TABLE 2

Selected Half Cell Reactions of the Wood-Ljungdahl Pathway.

| Half Cell Reduction | $\Delta G_r^o$ (kj/mol) | $E^o$ (mV) | $n_e$ | $\Delta m_H$ | $\Delta G_r^{o\prime}$ (kj/mol) | $E^{o\prime}$ (mV) | $\Pi_{prod}/\Pi_{react}$ |
|---|---|---|---|---|---|---|---|
| $2H^+ + 2e^- \leftrightarrow H_{2(g)}$ | 0 | 0 | 2 | -2 | 79.90 | -414 | $p_{H2}$ |
| $CO_2 + 2H^+ + 2e^- \leftrightarrow CO_{(g)} + H_2O$ | 20.03 | -104 | 2 | -2 | 99.93 | -518 | $p_{CO}/p_{CO2}$ |
| $CH_3CHO + 2H^+ + 2e^- \leftrightarrow CH_3CH_2OH$ | -41.85 | 217 | 2 | -2 | 38.05 | -197 | $C_{Et}/C_{Ald}$ |
| $CH_3COOH + 2H^+ + 2e^- \leftrightarrow CH_3CHO + H_2O$ | -7.67 | 40 | 2 | -2 | 72.23 | -374 | $C_{Ald}/C_{HA}$ |
| $NAD^+ + H^+ + 2e^- \leftrightarrow NADH$ | 21.80 | -113 | 2 | -1 | 61.75 | -320 | $C_{NADH}/C_{NAD+}$ |
| $Fd_{Ox} + 2e^- \leftrightarrow Fd_{Rd}$ | 81.05 | -420 | 2 | 0 | 81.05 | -420 | $C_{Fdr}/C_{Fdo}$ |

The electrochemical couples are defined by the mass action ratio of products to reactants in the half cells at given pH; the $CO/CO_2$ half-cell is defined by $p_{CO}*/p_{CO2}*$, but the $H_2$ half-cell is defined by $p_{H2}*$ alone. The calculated $p_{H2}*$ defines potential at given pH and is the best measure of the internal electrochemical potential, $E_{Cell}$, that sets the ratio of ethanol to acetic acid attained. Equation 18 correlates the concentrations of chemicals inside the cell to the intracellular pH ($pH_{ic}$) and $E_{Cell}$.

The partial pressure of dissolved $H_2$, $p_{H2}^*$ referred to the standard state pressure of 1 atm or 101.3 kPa, particularly defines $E_{Cell}$ at given $pH_{ic}$. The ratio of CO to $CO_2$, $p_{CO}^*/p_{CO2}^*$, similarly defines $E_{Cell}$, but this relationship is used in the model to calculate the dissolved pressure of CO, $p_{CO}^*$. For this ratio, $p_{CO}^*$ and $p_{CO2}^*$ can be in any pressure unit. However, the pressure of $H_2$, $p_{H2}^*$, must be in atm (or as kPa/101.3) for use in these calculations to reference the standard state for $H_2$ (1 atm). The model uses the assumption of a single cell potential ($E_{Cell}$) and intracellular pH ($pH_{ic}$) to calculate the mass action ratios for use in thermodynamic and kinetic calculations. If $pH_{ic}$ is known, $E_{Cell}$ can be calculated.

Equation 19 written for acetic acid reduction to acetaldehyde, and again for acetaldehyde reduction to ethanol (see Table 2), can predict the ratio of the concentration of ethanol to the concentration of free acetic acid $[CH_3COOH]$.

$$\frac{[CH_3CHO]}{[CH_3COOH]} \frac{[CH_3CH_2OH]}{[CH_3CHO]} = \frac{[CH_3CH_2OH]}{[CH_3COOH]} \quad (19)$$

Figure 3:
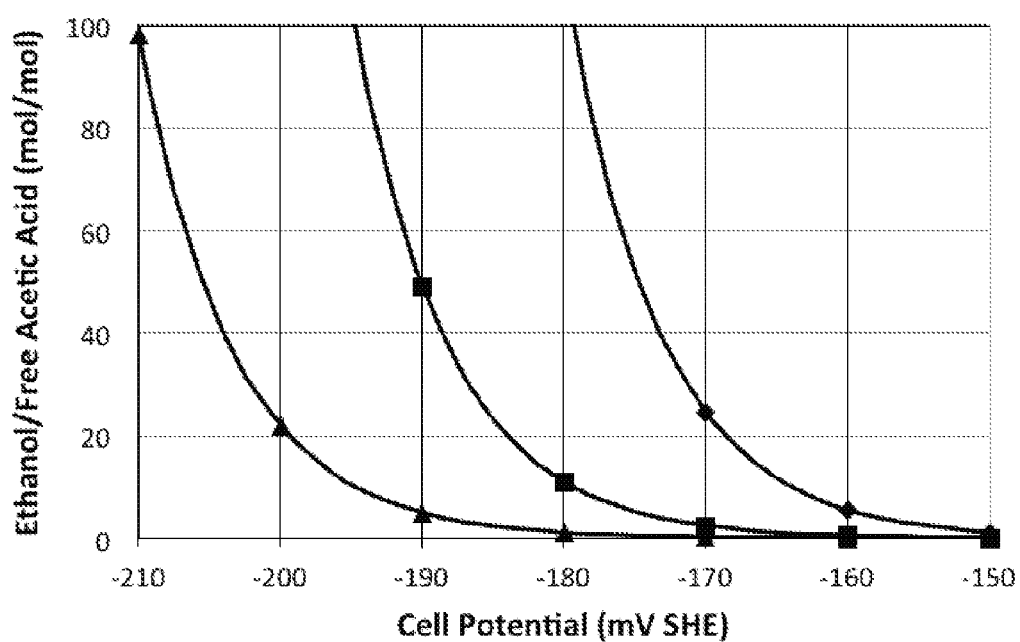
FIG. 3 provides a graph of the concentration ratio of ethanol to free acetic acid predicted in fermentation of syngas. $(C_{Et}/C_{HA})_{ic}$ ratio at intracellular redox potential for $pH_{ic}$ of 4.5 (♦), 4.75 (■), and 5.0 (▲).

This ratio is set by $E_{Cell}$ and $pH_{ic}$. The ratio of ethanol to free acetic acid inside the cell $(C_{Et}/C_{HA})_{ic}$, is shown versus $E_{Cell}$ in FIG. 3 at various $pH_{ic}$. The required potential is lower as $pH_{ic}$ rises, but very high ratios, greater than 100 mol/mol, are predicted at achievable potentials near the pH range used in fermentation with *C. ragsdalei*.

Estimation of $pH_{ic}$ and $E_{Cell}$

Equation 18 can be used for the redox couple written as reduction (Table 2) with $p_{H2}^*$ (in atm) and again with $C_{Et}/C_{HA}$ to derive an equation for the intracellular potential ($E_{Cell}$), as in Equations 20, 21 and 22. The unit "atm" is used in this calculation because the standard state for gas is 1 atm. Alternatively, $p_{H2}^*$ can be expressed in kPa as $(p_{H2}^*/101.3)$ for the calculation.

$$p_{H2}^* = \exp\left[-\frac{\Delta G_{r,H2}^\circ}{RT} - \frac{n_e F E_{Cell}}{RT} + 2.302 \Delta m_H pH_{ic}\right] \quad (20)$$

$$\left(\frac{C_{Et}}{C_{HA}}\right)_{ic} = \exp\left[-\frac{\Delta G_{r,EA}^\circ}{RT} - \frac{n_e F E_{Cell}}{RT} + 2.302 \Delta m_H pH_{ic}\right] \quad (21)$$

$$E_{Cell} = \frac{-(\ln p_{H2}^* + 4.604 pH_{ic})}{0.07484} = \frac{-\left(\ln\left(\frac{C_{Et}}{C_{HA}}\right)_{ic} - 19.20 + 9.208 pH_{ic}\right)}{0.14967} \quad (22)$$

The number of electrons transferred ($n_e$) is 2 in Equation 20 and 4 in Equation 21, and the number of protons released ($\Delta m_H$) is -2 and -4, respectively. Equation 22 can be simplified eliminating $pH_{ic}$ to relate $p_{H2}^*$ (in atm) and $(C_{Et}/C_{HA})_{ic}$ $$\ln\left(\frac{(p_{H2}^*)^2}{\left(\frac{C_{Et}}{C_{HA}}\right)_{ic}}\right) = -19.20 \quad (23)$$

For acetic acid, as a weak acid, the ratio of acetate to free acetic acid is $$\frac{C_{Ac}}{C_{HA}} = 10^{(pH-pK_a)} \quad (24)$$

And across the membrane:

$$\left(\frac{C_{Ac}}{C_{HA}}\right)_{ic}\left(\frac{C_{HA}}{C_{Ac}}\right) = 10^{(pH_{ic}-pH)} \quad (25)$$

Where ic represents the intracellular value of concentration of acetate ($CH_3COO^-$) and free acetic acid ($CH_3COOH$), and pH, and no subscript indicates the values measured outside the cell. Then, assuming that the ethanol concentration is the same inside and outside the cell, and assuming that acetate concentration is the same across the membrane, as for facilitated diffusion, $pH_{ic}$ can be obtained from Equation 26

$$pH_{ic} = pH + \log\left(\frac{C_{Et}}{C_{HA,ic}} \frac{C_{HA}}{C_{Et}}\right) \quad (26)$$

And combining Equations 23 and 26 to eliminate $(C_{Et}/C_{HA})_{ic}$ $$pH_{ic} = pH + \log\left(\frac{(p_{H2}^*)^2 e^{19.20}}{\left(\frac{C_{Et}}{C_{HA}}\right)}\right) \quad (27)$$

The internal pH ($pH_{ic}$) can be calculated from the dissolved $H_2$ (in atm), the external pH and the measured concentrations of ethanol and acetic acid in the fermentation broth. The accuracy of these results is subject to the error of the assumptions that allow the calculation. The ethanol concentration will change slightly across the membrane, but the assumption of facilitated transport of acetate to equalize the concentration across the membrane is advanced to address the chemical potential created by the pH difference near the $pK_a$ of acetic acid. The calculated $pH_{ic}$ can be entered in Equation 22 to obtain the intracellular potential, $E_{Cell}$.

Experimental Results and Discussion

Fermentation Control

Calculation of $k_{L,CO} a/V_L$, $k_{L,H2} a/V_L$, $k_{L,CO2} a/V_L$, $p_{CO}^*$, $p_{H2}^*$ and $p_{CO2}^*$ was coded in an Excel spreadsheet, and used to guide fermentation in a CSTR using a model syngas mix. The controlled fermentation has achieved up to 95% conversion of both CO and $H_2$ simultaneously, and has been used to define the kinetic parameters for the acetogenic culture, *Clostridium ragsdalei*, used in experiments SGIE1 through SGIE7 (Table 3).

TABLE 3

Summary of syngas fermentations in the CSTR

| Experiment | SGIE1 | SGIE2 | SGIE3 | SGIE4 | SGIE5 | SGIE6 | SGIE7 |
|---|---|---|---|---|---|---|---|
| Gas flow (sccm) | 75 | 38.2 | 17.5 | 17.7 | 17.7 | 17.7 | 17.7 |
| vvm[a] | 0.030 | 0.015 | 0.008 | 0.008 | 0.008 | 0.008 | 0.008 |
| Max. Agitation (rpm) | 400 | 600 | 280 | 650 | 900 | 700 | 400 |
| Cumulative CO and $H_2$ Uptake (mmol) | 1042 | 1573 | 1600 | 1900 | 1680 | 1700 | 1000 |
| Cell Conc (mg/L) | 270 | 320 | 328 | 304 | 350 | 310 | 270 |
| Ethanol (g/L) | 0.1 | 0.13 | 0.09 | 0.13 | 0.19 | 0.24 | 1.05 |
| Acetic acid (g/L) | 6.0 | 6.6 | 7.0 | 7.0 | 6.6 | 6.7 | 5.0 |
| Max CO conversion (%) | 36 | 86 | 68 | 92 | 95 | 95 | 71 |
| Max $H_2$ Conversion (%) | 0 | 82 | 75 | 94 | 96 | 95 | 77 |
| Max $k_{L,CO}a/V_L$ ($h^{-1}$) | 52 | 87 | 22.5 | 46.3 | 63.8 | 73.6 | 23.0 |
| at G (sccm)[b] | 75 | 38.2 | 17.5 | 17.7 | 19.4 | 20.3 | 17.7 |
| at N (rpm)[b] | 400 | 600 | 280 | 650 | 900 | 700 | 300 |

[a] vvm is volume of gas per volume of liquid per minute
[b] G is gas flow and N is agitation speed for maximum $k_{L,CO}a/V_L$

*C. ragsdalei* was grown in the CSTR in seven experimental runs and the results are summarized in Table 3. Calculation of $k_{L,CO}$ $a/V_L$, $k_{L,H2}$ $a/V_L$, $k_{L,CO2}$ $a/V_L$, $p_{CO}^*$, $p_{H2}^*$ and $p_{CO2}^*$ was used in each run to maintain consumption of $H_2$ as a significant portion of the total gas used. Fermentation started with low cell concentration and limited kinetic capacity to convert CO and $H_2$. The gas flow was set at a rate that was expected to be mostly converted in later fermentation, and with low agitation of 150 rpm to reduce mass transfer until uptake of both CO and $H_2$ was established. This procedure reduces inhibition of the culture by oversupply of gas and reduces the lag phase before cell growth starts.

Figure 4:
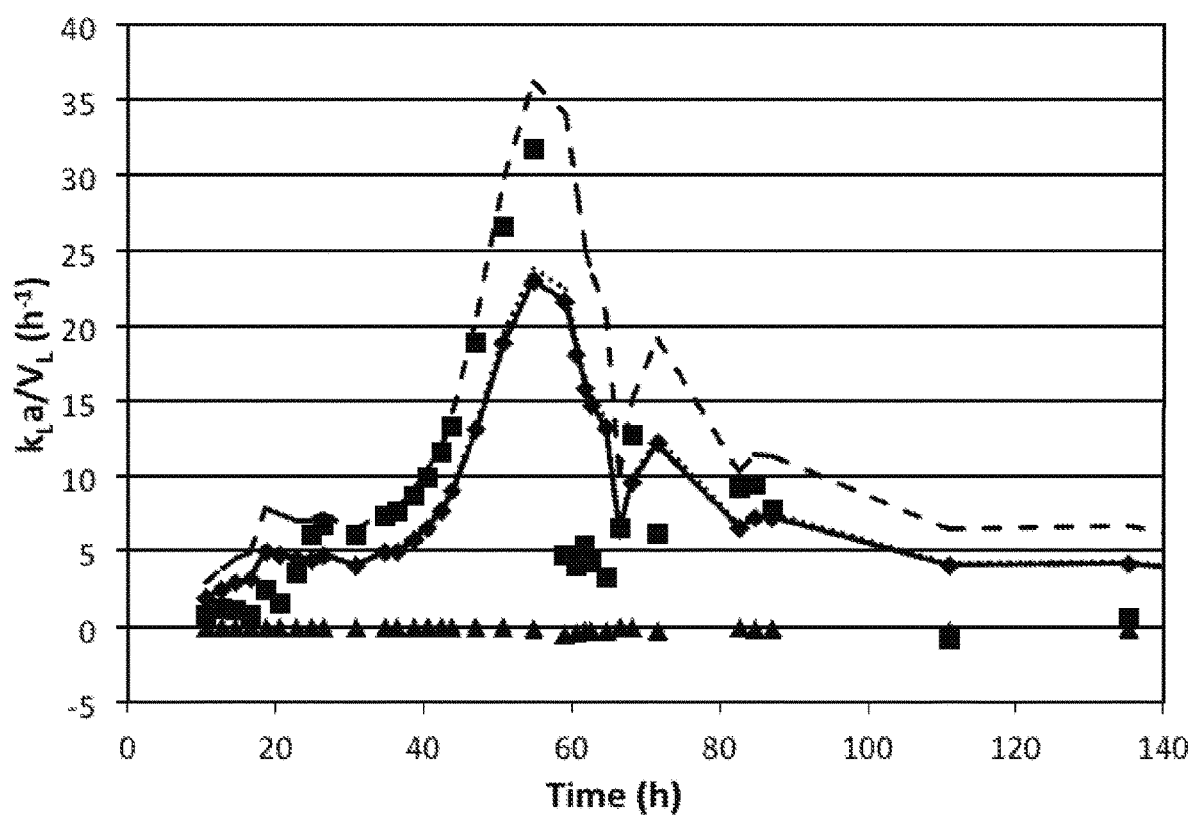
FIG. 4 provides a graph of volumetric mass transfer coefficients for CO, $H_2$ and $CO_2$ in CSTR fermentation of syngas SGIE7. Apparent $k_{La}/V_L$ for CO (♦), $H_2$ (■), $CO_2$ (▲), and predicted capacity for CO (—), $H_2$ (_ _), and $CO_2$ ( . . . ).

Once growth begins, the dissolved gas concentrations are low and the culture aggressively consumes both CO and $H_2$ to derive energy for production of cell materials. The fermentation quickly becomes mass transfer limited and the agitation must be increased to supply more gas to feed the increasing cell mass. Energy is required in the form of ATP and as reduced intracellular electron carriers, such as nicotinamide adenine dinucleotide (NADH), flavin adenine dinucleotide ($FADH_2$) and ferredoxin (Fd). Mass transfer in the CSTR is characterized by the overall volumetric mass transfer coefficient ($k_La/V_L$) for each gas species, CO, $H_2$ and $CO_2$. The apparent $k_La/V_L$ values were calculated for CO, $H_2$ and $CO_2$ from the observed gas uptake and compositions of the inlet and effluent gas over the course of fermentation using Equation 5 for each gas assuming that $p_{CO}^*$, $p_{H2}^*$ and $p_{CO2}^*$ are zero as in Equation 7. The apparent $k_La/V_L$ is the mass transfer coefficient calculated when mass transfer limitation is assumed. CO is assumed to be mass transfer limited and the apparent $k_{L,CO}$ $a/V_L$ is assumed to equal the actual $k_{L,CO}$ $a/V_L$ whenever fermentation is active, particularly when $H_2$ is consumed. The value of $k_{L,CO}$ $a/V_L$ observed in FIG. 4 sets the expectation of mass transfer capacity for all gases through Equation 8. The predicted $k_{L,CO2}$ $a/V_L$ by Equation 8 and shown in FIG. 4 is 4% higher than $k_{L,CO}a/V_L$. However, the observed or apparent $k_{L,CO2}$ $a/V_L$ is near zero. Little transfer of $CO_2$ is observed as there is only small molar production of $CO_2$ and the liquid is saturated at the concentration in equilibrium with $CO_2$ in the effluent gas. The apparent $k_{L,H2}$ $a/V_L$ is within 10% of that predicted from $k_{L,CO}$ $a/V_L$ using Equation 8 between 23 and 55 h of fermentation (FIG. 4). After 55 h the apparent $k_{L,H2}$ $a/V_L$ is lower than the predicted value, except when the agitation or gas feed rate is adjusted after 64 and 72 h. This indicates that scaling $k_{L,CO}$ $a/V_L$ using the square root of the ratio of the diffusivities for CO and $H_2$ is valid, and that after 55 h the available capacity for transfer of $H_2$ is not used efficiently. The loss of $H_2$ efficiency is likely the result of accumulation of CO greater than $7 \times 10^{-9}$ mol/L in the fermentation broth that inhibits the hydrogenase enzyme.

Figure 5:
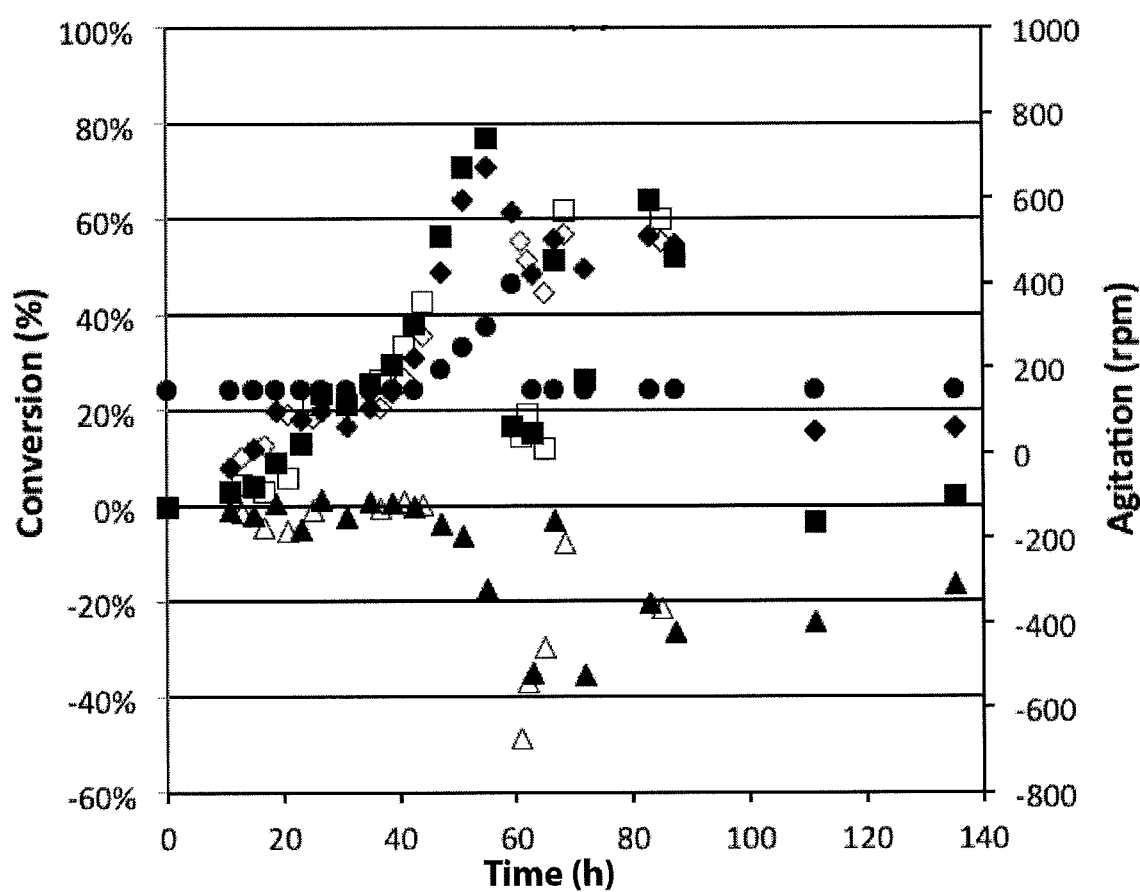
FIG. 5 provides a graph of gas conversions and agitation in CSTR fermentation of syngas SGIE7. CO (♦), —$H_2$ (■), $CO_2$ (▲) and agitation (●). Open symbols are data when only a gas sample was taken.

FIG. 5 shows the conversions of CO and $H_2$ achieved in the course of the fermentation, the production of $CO_2$ denoted as negative conversion and the agitation speed. Initial conversion is low and is limited to CO through about 18 h. However, $H_2$ conversion begins at about 20 h and quickly increases to exceed percent conversion of CO by 30 h with agitation speed of 150 rpm. The agitation speed was increased incrementally from 150 rpm at 40 h to 400 rpm at 55 h. Each increase in agitation speed increased the gas conversion, up to 72% for CO and 77% for $H_2$, until the last increase from 300 to 400 rpm precedes a drop of CO conversion to 62% and $H_2$ conversion to only 18%. After 60 h of fermentation the agitation speed was maintained at 150 rpm. Conversion of $H_2$ and CO was recovered by reducing gas flow (FIG. 6) from 17.5 to 7.1 sccm at 64 h, and again from 14.1 to 7.1 sccm at 72 h.

Figure 6:
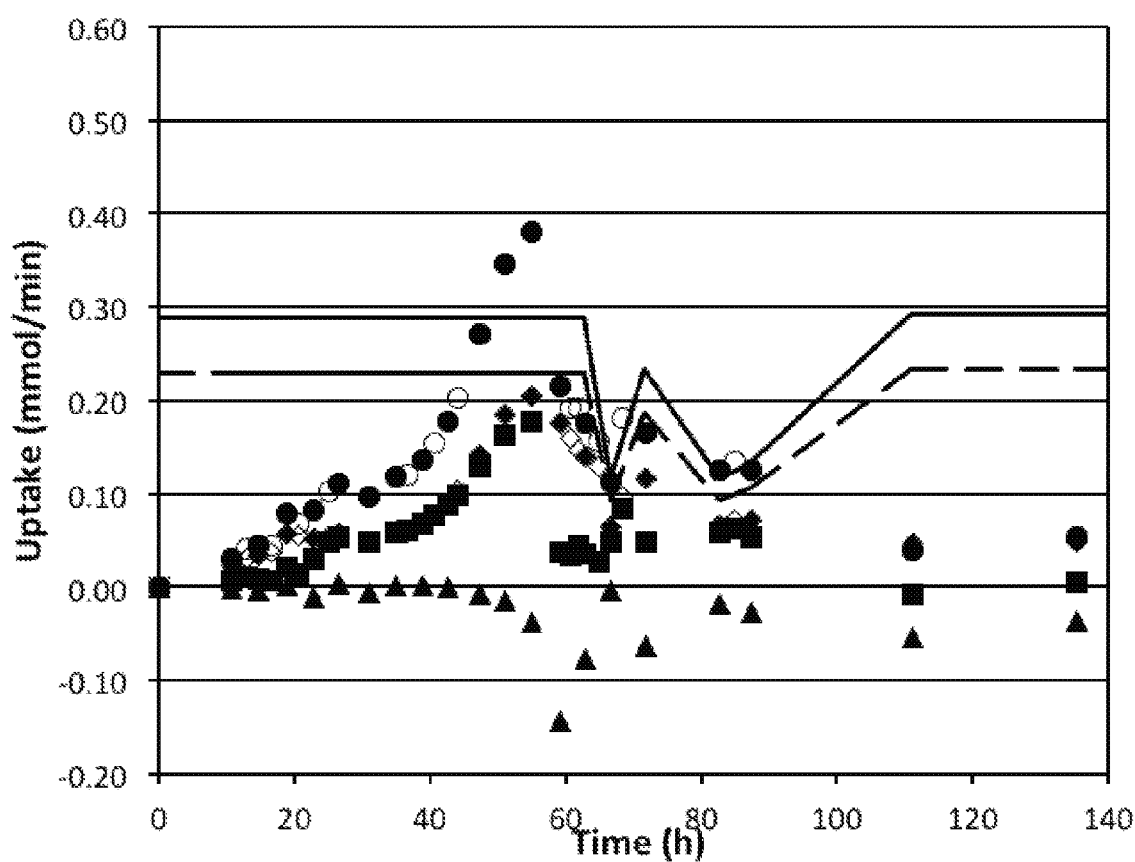
FIG. 6 provides a graph of gas uptake in CSTR fermentation of syngas SGIE7. CO (♦), $H_2$ (■), $CO_2$ (▲), CO+$H_2$ (●), CO feed rate (—) and $H_2$ feed rate (_ _). Open symbols are data when only a gas sample was taken.

The molar uptake of CO, $H_2$ and sum of both ($CO+H_2$), and the inlet molar flow rates of CO and $H_2$ are shown in FIG. 6. The gas uptake follows the course seen in conversion, and the highest total uptake occurs at 55 h before the agitation is increased to 400 rpm and the $H_2$ conversion is diminished. $H_2$ uptake recovered slightly after the feed gas rate was cut at 64 h, but remained low through the rest of the fermentation. CO uptake also diminished after 55 h.

Figure 7:
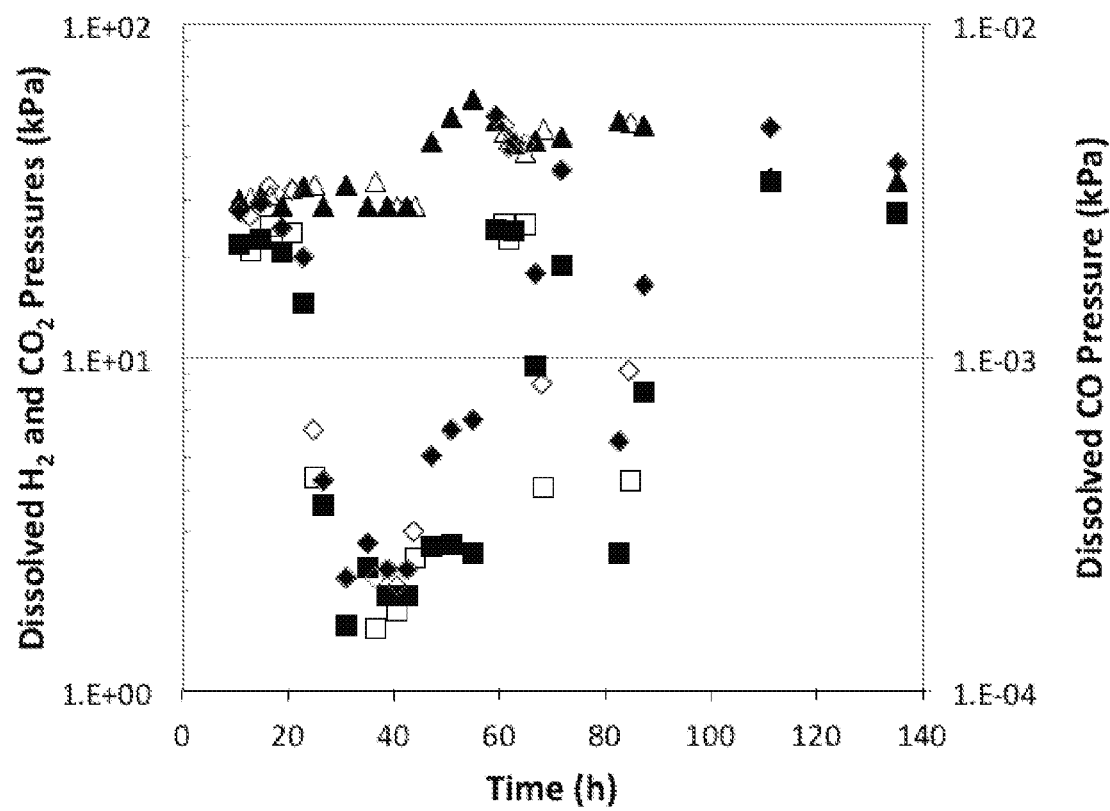
FIG. 7 provides a graph of partial pressures of dissolved CO, $H_2$ and $CO_2$ in CSTR fermentation of syngas SGIE7. CO (♦), $H_2$ (■) and $CO_2$ (▲) Open symbols are data when only a gas sample was taken.

The bulk liquid concentrations of dissolved gases, shown as the equilibrium partial pressure using Henry's Law (Equation 2), are plotted in FIG. 7. The calculation has large potential error (orders of magnitude) when $H_2$ is not converted, as $p_{CO}^*$ is calculated from the pressure of $H_2$ in the bulk liquid ($p_{H2}^*$), but $p_{CO}^*$ is in equilibrium with the effective $H_2$ pressure that is generally less than $p_{H2}^*$ when the hydrogenase enzyme is inhibited by CO. $H_2$ is not converted before 20 h and after 90 h of this fermentation. The dissolved CO pressure can be higher or lower than that calculated, as the equilibrium of the water gas shift reaction (Equation 11) has not been established.

However, as $H_2$ conversion is established after 20 h of fermentation, the equilibrium of the water gas shift reaction is established inside the cells, $k_{L,CO}$ $a/V_L$ is more certain, and dissolved pressures can be calculated with good confidence. Here, "good confidence" denotes values of acceptable accuracy to be useful in scientific and engineering calculations, in some cases±orders of magnitude. Note that $p_{CO}*$ is less than $p_{H2}*$ and $p_{CO}*$ by about 4 orders of magnitude (a factor of $10^{-4}$). This supports the assumption of CO mass transfer to an arithmetic zero. The value of $p_{CO}*$ that inhibits the hydrogenase enzyme can be estimated from FIG. 7 to be about $10^{-3}$ kPa, above which $H_2$ uptake is decreased.

Figure 8:
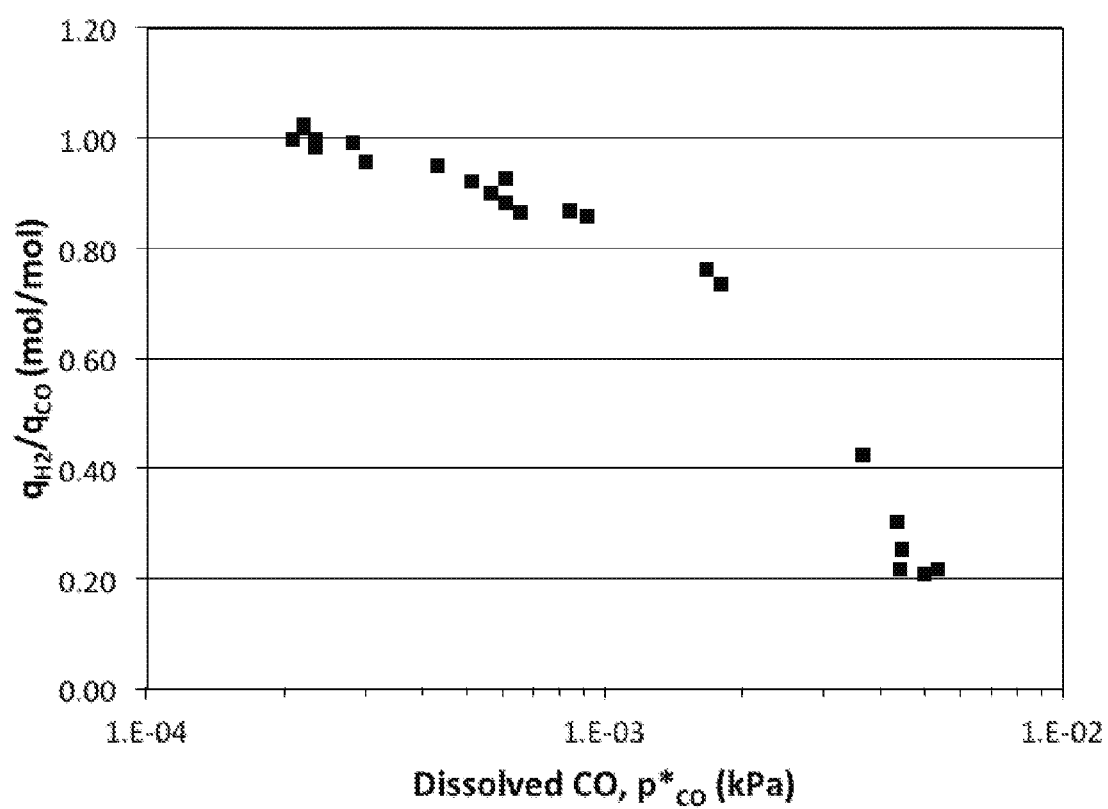
FIG. 8 provides a graph of the ratio of $H_2$ uptake to CO uptake versus dissolved CO in CSTR fermentation of syngas SGIE7.

The inhibition of $H_2$ uptake rate is further illustrated in FIG. 8, which depicts the ratio of $H_2$ to CO uptake as a function of dissolved CO. $H_2$ partial pressure in the gas phase is high when the rate of uptake is low, so the actual concentration in the liquid will be high and near saturation. At the same time, the uptake of CO is relatively high, suggesting that sufficient cell mass and hydrogenase enzyme is present to effect the conversion of $H_2$ proportional to the CO conversion. The dissolved $H_2$ pressure, $p_{H2}*$, is high when $H_2$ is not consumed and high $H_2*$ should increase the reaction consuming $H_2$. However, increased $H_2$ uptake is not observed until $p_{CO}*$ falls below $2 \times 10^{-3}$ kPa, and $H_2$ also falls as a consequence of consumption. These observations clearly imply CO inhibition of hydrogenase above $10^{-3}$ kPa dissolved CO pressure. Inhibition of the hydrogenase enzyme lessens gradually as $p_{CO}*$ decreases.

Figure 9:
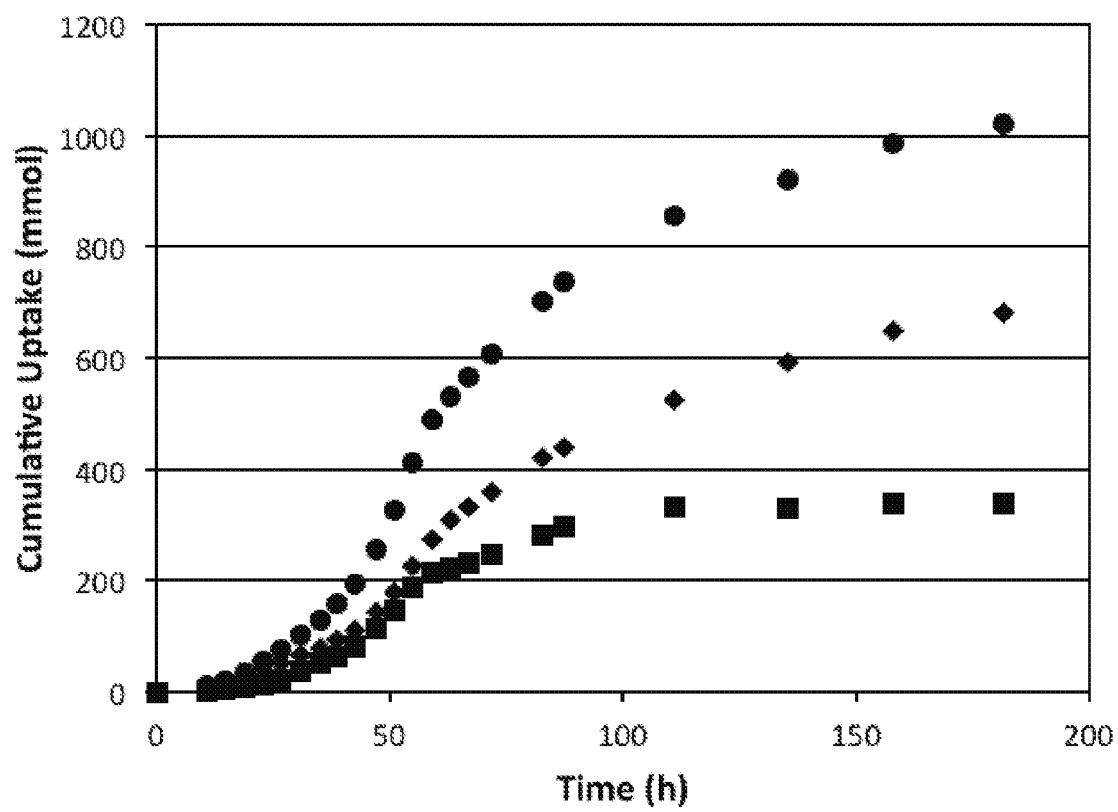
FIG. 9 provides a graph of cumulative uptake in CSTR fermentation of syngas SGIE7. CO (♦), $H_2$ (■), COs+$H_2$ (●).

The cumulative uptake of the energy substrates CO and $H_2$ over the course of this fermentation (SGIE7) in the CSTR is shown in FIG. 9. CO and $H_2$ are consumed for the first 110 h of the fermentation, with slow consumption of CO from 110 to 180 h. The fermentation was followed through 350 h, with little additional uptake of CO or $H_2$. A total of 1000 mmol of CO plus $H_2$ was consumed by the culture over 182 h.

Figure 10:
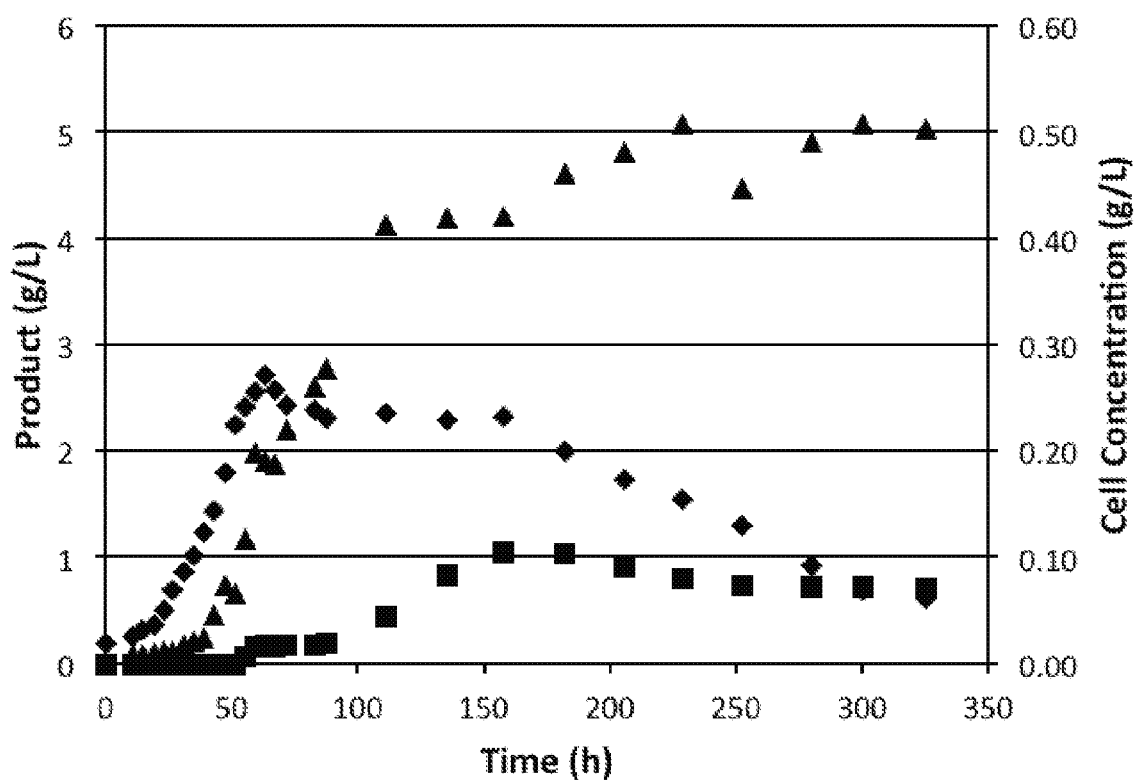
FIG. 10 provides a graph of cells and products concentrations in CSTR fermentation of syngas SGIE7. Ethanol (■), acetic acid (▲), cells (♦).

The products of the fermentation are shown in FIG. 10, with the primary product being acetic acid. About 1 g/L of ethanol was produced between 50 h and 150 h of the fermentation. Cell concentration of 0.27 g of cells per liter ($g_x$/L) was achieved. Cell concentration peaked at 55 h of the fermentation, coincident with the loss of $H_2$ conversion. This indicates that a nutrient limitation was reached that slowed growth and energy demand to support growth. The slower uptake indicates onset of a kinetic limitation that limits the rate of gas conversion. Mass transfer, which should have increased with the increased agitation speed to 400 rpm at 54 h, exceeded the capability of the culture to consume the CO and $H_2$, CO accumulated in the fermentation broth and $H_2$ uptake was reduced from CO inhibition.

The data shown in FIGS. 4 through 10 represent SGIE7, which was one of seven fermentations run in a 3 L CSTR to assess the batch fermentation, gain skill in operation and develop the control strategy. Analysis of syngas fermentation in the CSTR used a mathematical model to guide control decisions regarding agitation intensity and feed gas flow. Over 90% conversion of both CO and $H_2$ was achieved in three of these fermentations with agitation speeds of 650, 700 and 900 rpm; $k_{L,CO} a/V_L$ up to 74 $h^{-1}$ was demonstrated (at 700 rpm). The inhibition of $H_2$ uptake by CO followed a similar pattern for all fermentations, with inhibition of hydrogenase above $10^{-3}$ kPa dissolved CO pressure.

Estimation of Intracellular $pH_{ic}$ and Potential $E_{Cell}$

The intracellular $pH_{ic}$ and potential ($E_{Cell}$) calculated for external pH values of 5.0 and 4.5 are shown in Table 4 for varied dissolved $H_2$ (inside and outside the cell) and $C_{Et}/C_{HA}$ outside the cell. In Table 4, $p_{H2}*$ and $C_{Et}/C_{HA}$ are specified, then $pH_{ic}$ is calculated using Equation 27, and $E_{Cell}$ is finally calculated from $pH_{ic}$ using Equation 22. The indicated $pHi_c$ is the pH that provides equilibrium with the specified $C_{Et}/C_{HA}$ at that specified $p_{H2}*$. $E_{Cell}$ is already determined when $pH_{ic}$ and $p_{H2}*$ are known.

As an example, for a $p_{H2}*$ of 0.01 atm and $C_{Et}/C_{HA}$ of 1.0 with external pH of 5.0, $pH_{ic}$ is 9.34 shown as bold and underlined in Table 4. If $pH_{ic}$ was lower than 9.34 the thermodynamic expectation would be that $p_{H2}*$ would decrease and $C_{Et}/C_{HA}$ would increase to achieve equilibrium.

In a second example, as $C_{Et}/C_{HA}$ increases from 1 to 100 when $p_{H2}*$ increases from 0.0001 to 0.001 (kPa/101.3) and the $pH_{ic}$ is 5.34 for external pH of 5.0; the value of $E_{Cell}$ decreases from −205 to −236 mV (see the plain underlined data with external pH at 5.0). With an external pH of 4.5, $C_{Et}/C_{HA}$ again increases from 1 to 100 when $p_{H2}*$ increases from 0.0001 to 0.001 (kPa/101.3); however, the $pH_{ic}$ is 4.84 and the value of $E_{Cell}$ decreases from −175 to −205 mV (see the plain underlined data with external pH of 4.5).

In a third contrasting example, as $C_{Et}/C_{HA}$ increases from 0.01 to 1000 when $p_{H2}*$ increases from 0.0001 to 0.01 (kPa/101.3), the $pH_{ic}$ decreases from 6.84 to 5.84 even though the value of $E_{Cell}$ remains at −298 mV (see the bold italic data with external pH of 4.5).

TABLE 4

Intracellular pH and potential from $p_{H2}*$. The ratio of ethanol to free acetic acid outside the cell $C_E/C_{HA}$ is varied at pH 5.0 or 4.5 outside the cell.

| $p_{H2}*$ (kPa/101.3) | 0.1 | 0.01 | 0.001 | 0.0001 |
|---|---|---|---|---|
| pH = 5 | | | | |
| $C_E/C_{HA}$ (mol/mol) | | $pH_{ic}$ (from Equation 27) | | |
| 0.01 | 13.34 | 11.34 | 9.34 | 7.34 |
| 0.1 | 12.34 | 10.34 | 8.34 | 6.34 |
| 1 | 11.34 | 9.34 | 7.34 | <u>5.34</u> |
| 10 | 10.34 | 8.34 | 6.34 | 4.34 |
| 100 | 9.34 | 7.34 | <u>5.34</u> | 3.34 |
| 1000 | 8.34 | 6.34 | 4.34 | 2.34 |
| $C_E/C_{HA}$ (mol/mol) | | $E_{cell}$ (mV SHE) (from Equation 22) | | |
| 0.01 | −790 | −636 | −482 | −328 |
| 0.1 | −728 | −574 | −421 | −267 |
| 1 | −667 | −513 | −359 | <u>−205</u> |
| 10 | −605 | −451 | −298 | −144 |
| 100 | −544 | −390 | <u>−236</u> | −82 |
| 1000 | −482 | −328 | −175 | −21 |
| pH = 4.5 | | | | |
| $C_E/C_{HA}$ (mol/mol) | | $pH_{ic}$ (from Equation 27) | | |
| 0.01 | 12.84 | 10.84 | 8.84 | *6.84* |
| 0.1 | 11.84 | 9.84 | 7.84 | 5.84 |
| 1 | 10.84 | 8.84 | 6.84 | <u>4.84</u> |
| 10 | 9.84 | 7.84 | 5.84 | 3.84 |
| 100 | 8.84 | 6.84 | <u>4.84</u> | 2.84 |
| 1000 | 7.84 | *5.84* | 3.84 | 1.84 |
| $C_E/C_{HA}$ (mol/mol) | | $E_{cell}$ (mV SHE) (from Equation 22) | | |
| 0.01 | −759 | −605 | −451 | *−298* |
| 0.1 | −698 | −544 | −390 | −236 |
| 1 | −636 | −482 | −328 | <u>−175</u> |
| 10 | −574 | −421 | −267 | −113 |
| 100 | −513 | −359 | <u>−205</u> | −52 |
| 1000 | −451 | *−298* | −144 | 10 |

The data in these examples show the dependence of $C_{Et}/C_{HA}$ on the combination of $pH_{ic}$ and $E_{Cell}$. Internal pH of 5.6 with a potential difference across the membrane of 80 mV (low E inside) was reported at an external pH of 5.0 for

*Clostridium thermoacelicum* grown on glucose (Baronofsky et al., 1984). This is similar to the differences in Table 4. The value $p_{H2}*$ from experiment are 1 kPa ($10^{-2}$ atm) and up, higher than the pressures predicted by Table 4 for $pH_{ic}$ of 5.0 to 6.0. This suggests that effective $p_{H2}*$ is lower than the $p_{H2}*$ estimated in analysis of the current experiments, and that inhibition of hydrogenase still decreases the efficiency of $H_2$ in current fermentation practice.

In the fermentation of pure substrates $CO/CO_2$ and $H_2/CO_2$ in batch bottles with *C. ljungdahli*, uptake of $H_2$ was slightly faster (mol/h) with lower cell concentration than for fermentation with $CO/CO_2$ (Phillips et al., 1994). The CSTR fermentation presented here is as yet CO inhibited with $p_{CO}*$ above $2 \times 10^{-4}$ kPa, and the untapped $H_2$ could provide more ethanol with greater conservation of energy if the fermentation control is refined. The processing of $H_2$ on the hydrogenase enzyme is slowed by CO inhibition, and the water gas shift analysis is in error as the full potential of dissolved $H_2$ is not available. The inhibition produces a lower effective $H_2$ pressure that is consistent with the measured product ratio.

Model Summary

Our conceptual model of the syngas fermentation is developed from the physical processes like mass transfer of CO and $H_2$, structure of the cell and configuration of the equipment, and the mechanisms used in the transformation of gas to product.

The reactions of the Wood-Ljungdahl pathway define the stoichiometry, and the expected mass balance is generally confirmed in the observed results. Mass transfer of CO and $H_2$ is driven by concentration differences that are sustained by reaction. Fermentation kinetic parameters are set by one or two limiting reaction rates. The overall currents of carbon, protons and electrons through the reaction circuits are set by these limited rates and determine the products of fermentation.

Mass transfer is described mathematically by assuming limitation of transfer for CO, with transfer to essentially zero concentration in the bulk liquid and cells. The mass transfer is characterized as $k_{L,CO} \, a/V_L$ and scaled to determine the capacity to transfer $H_2$ and $CO_2$. The concentrations of dissolved CO, $CO_2$ and $H_2$ inside the cell at the sites of reaction in the enzymes are calculated using the defined mass transfer capacities and assuming the water gas shift is in equilibrium. The calculated concentrations of CO, $H_2$ and $CO_2$ can be used in kinetic and thermodynamic calculations to define the fermentation.

The supply of CO via the applied mass transfer can inhibit the uptake of $H_2$. $H_2$ is an effective driver of production if not inhibited. When CO inhibition is low, indicated by consumption of $H_2$, the concentration of dissolved $H_2$ and intracellular pH define the electrochemical potential inside the cell. Important reactions involved in the pathway of production are oxidation reduction reactions that are driven by the cell potential. This potential poises these significant reactions near thermodynamic equilibrium with $\Delta G_r = 0$, and this boundary condition allows calculation of conditions in the cell. The ratio of ethanol to free acetic acid is a key and measurable parameter defined by these calculations. The predictions of the model are supported by the ratio of ethanol to acetic acid measured in the fermentation.

No net ATP to support cell growth is produced by the reactions of the Wood-Ljungdahl pathway; unlike growth on glucose that produces 2 ATP in production of 2 acetyl CoA (Tracy et al., 2012). Autotrophic growth of acetogens is dependent on ATP formed by an ATPase via a chemiosmotic mechanism (Cramer and Knaff, 1991). The ATPase is driven by the protonmotive force that results from the combination of the potential difference and the pH difference across the cell membrane as in Equation 28 (Cramer and Knaff, 1991).

$$\Delta p = \Delta \psi - \frac{2.3RT}{F} \Delta pH \qquad 28$$

The protonmotive force, $\Delta p$, forces conformation change in the ATPase that frees ATP to the cell. The potential difference, $\Delta \psi$, is the difference of the intracellular potential, $E_{Cell}$ and the ORP measured in the bulk liquid, and the pH difference ($\Delta pH$) is between the calculated intracellular $pH_{ic}$ and the measured bulk liquid pH. The calculation of and potential inside the cell make possible the study of growth supported by ATPase embedded in the membrane (Das and Ljungdahl, 1997; Ivey and Ljungdahl, 1986; von Ballmoos et al., 2008). Further, ethanol production is seen to begin as growth slows and when ATP would be expected to accumulate. The accumulation of ATP will affect both pH and potential inside the cell, and affect the production of ethanol relative to acetic acid. Our model is a tool to better understand this transition that is critical to biofuel production.

CONCLUSIONS

The mass balance from syngas fermentation agreed well with that expected from the stoichiometry of the production pathway, and the measured rates of CO and $H_2$ uptake feed the mass transfer calculations. Assumption of equilibrium thermodynamics, in particular equilibrium of the water gas shift reaction, inside the cells gave explicit equations for the concentrations of CO, $H_2$ and $CO_2$ at the enzyme active sites inside the cells. The calculated concentrations of reactants are appropriate for thermodynamic and kinetic calculations. Application of the model in analysis of syngas fermentation gave estimates of the CO, $H_2$ and $CO_2$ dissolved pressures consistent with the assumptions of the model development, and particularly showed dissolved CO at $2 \times 10^{-3}$ kPa partial pressure inhibits hydrogenase in *C. ragsdalei*. Calculation of dissolved CO was used to successfully control agitator speed and gas feed rate to maintain high energy conservation and culture activity in syngas fermentation. The model was extended to calculate the intracellular pH and electrochemical potential in syngas fermentation. These values can be combined with pH and ORP measured in the bulk fermentation broth to define membrane potentials useful in future growth and kinetics studies.

The invention of the present disclosure is not to be limited in its application to the details of the construction and to the arrangements of the components set forth in the preceding description or illustrated in the drawings. Rather, the invention is capable of other embodiments and of being practiced and carried out in various other ways not specifically enumerated herein. Finally, it should be understood that the phraseology and terminology employed herein are for the purpose of description and should not be regarded as limiting, unless the specification specifically so limits the invention.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

For purposes of the instant disclosure, the term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Terms of approximation (e.g., "about", "substantially", "approximately", etc.) should be interpreted according to their ordinary and customary meanings as used in the associated art unless indicated otherwise. Absent a specific definition and absent ordinary and customary usage in the associated art, such terms should be interpreted to be ±10% of the base value.

When, in this document, a range is given as "(a first number) to (a second number)" or "(a first number)-(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Further, it should be noted that terms of approximation (e.g., "about", "substantially", "approximately", etc.) are to be interpreted according to their ordinary and customary meanings as used in the associated art unless indicated otherwise herein. Absent a specific definition within this disclosure, and absent ordinary and customary usage in the associated art, such terms should be interpreted to be plus or minus 10% of the base value.

Still further, additional aspects of the instant invention may be found in one or more appendices attached hereto and/or filed herewith, the disclosures of which are incorporated herein by reference as if fully set out at this point.

Nomenclature $C_{i,L}$—molar concentration of i in liquid (mol/L)
CSTR—continuously stirred tank reactor
D—impeller diameter in CSTR (mm)
$D_{i,W}$—diffusivity of gas i in water
dn/dt—molar rate of transfer of gas species i (CO, $H_2$, $CO_2$)
E—electrochemical potential of redox couple at actual conditions (mV)
$E^0$—standard midpoint potential of redox couple, pH=0 (mV)
$E^{0'}$—standard midpoint potential of redox couple, pH=7 (mV)
$E_{Cell}$—intracellular electrochemical potential or ORP (mV)
F—Faraday constant (96.485 J/mV mol $e^-$)
G—gas flow (sccm)
$H_i$—Henry's Law constant for gas i (kPa L/mol)
*—denotes a quantity derived from the Henry's law equilibrium
$k_{L,i}a/V_L$—volumetric mass transfer coefficient for gas i (i can represent $O_2$, CO, $H_2$ or $CO_2$)
$k_L$—liquid film mass transfer coefficient
a—area of the gas liquid interface
$V_L$—liquid volume into which gas is transferred
L—liquid flow (L/h)
N—agitation speed (rpm)
$n_e$—number of electrons transfer in half cell reaction
ORP—oxidation reduction potential versus the standard hydrogen electrode (mV SHE)
$pH_{ic}$—intracellular pH
$p_i$—partial pressure of gas i (kPa),
$p_i^*$—partial pressure of dissolved gas by Henry's Law
$P_T$—pressure, total (kPa)
$q_i$—specific uptake rate of gas i (mol/$g_x$ h)
t—time (s, min, h)
$t_d$—doubling time for cell growth (h)
R—gas constant (8.314 J/mol K)
T—temperature (K)
vvm—volume of gas per volume of liquid per minute
X—cell concentration ($g_x$/L)
$y_i$—molar fraction of gas i in gas phase
$\Delta G_r$—Gibbs free energy change of reaction (kJ/mol)
$\Delta G^0$—Gibbs free energy change at standard conditions including pH=0 (kJ/mol)

$\Delta G^{0'}$—Gibbs free energy change at standard conditions including pH=7 (kJ/mol)

μ—specific growth rate ($g_x/g_x$ h or h$^{-1}$)

α—exponent of gas flow in correlation

β—exponent of power input in correlation $\Delta m_H$—number of protons released in oxidation reduction reaction Δp—protonmotive force (mV)

ΔpH—pH differential across the membrane

Δψ—potential difference (mV) across the membrane

Π—product of products and reactants in reaction mass action ratio

REFERENCES

Adams, S. S., S. Scott and C-W Ko. 2010. Method for Sustaining Microorganism Culture in Syngas Fermentation Process in Decreased Concentration or Absence of Various Substrates.

Bailey, J. E., Ollis, D. F. 1986. *Biochemical Engineering Fundamentals*. 2nd ed. McGraw-Hill, New York, Bakker, A., Smith, J. M., Myers, K. J. 1994. How to Disperse Gases in Liquids. Chemical Engineering, 101 (12), 98-104.

Baronofsky, J. J., Schreurs, W. J. A., Kashket, E. R. 1984. Uncoupling by Acetic Acid Limits Growth of and Acetogenesis by *Clostridium Thermoaceticum*. Applied and Environmental Microbiology, 48 (6), 1134-1139.

Bird, R. B., Stewart, W. E., Lightfoot, E. N. 2002. Transport Phenomena. 2nd ed, J. Wiley. New York, pp. xii, 895 p.

Boghigian, B. A., Shi, H., Lee, K., Pfeifer, B. A. 2010. Utilizing Elementary Mode Analysis, Pathway Thermodynamics, and a Genetic Algorithm for Metabolic Flux Determination and Optimal Metabolic Network Design. Bmc Systems Biology, 4.

Charpentier, J.-C. 1981. Mass-Transfer Rates in Gas-Liquid Absorbers and Reactors. in: *Advances in Chemical Engineering*, (Eds.) G. R. C. J. W. H. Thomas B. Drew, V. Theodore, Vol. Volume 11, Academic Press, pp. 1-133.

Cramer, W. A., Knaff, D. B. 1991. Energy Transduction in Biological Membranes: A Textbook of Bioenergetics. Springer study ed. in: *Springer advanced texts in chemistry*, Springer-Verlag. New York, pp. xiv, 579 p.

10 Das, A., Ljungdahl, L. G. 1997. Composition and Primary Structure of the FM Atp Synthase from the Obligately Anaerobic Bacterium *Clostridium Thermoaceticum*. Journal of Bacteriology, 179 (11), 3746-3755.

Drake, H. L., Gossner, A. S., Daniel, S. L. 2008. Old Acetogens, New Light. in: *Incredible Anaerobes: From Physiology to Genomics to Fuels*, (Eds.) J. Wiegel, R. J. Maier, 15 M. W. W. Adams, Vol. 1125, pp. 100-128.

Gaddy, J. L., D. K. Arora, C-W Ko, J. R. Phillips, R. Basu, C. V. Wikstrom and E. C. Clausen. 2007. Methods for Increasing the Production of Ethanol from Microbial Fermentation. 7285402.

Garcia-Ochoa, F., Gomez, E. 2009. Bioreactor Scale-up and Oxygen Transfer Rate in Microbial Processes: An Overview. Biotechnology Advances, 27 (2), 153-176.

Henry, C. S., Broadbelt, L. J., Hatzimanikatis, V. 2007. Thermodynamics-Based Metabolic Flux Analysis. Biophysical Journal, 92 (5), 1792-1805. Hougen, O. A., Watson, K. M., Ragatz, R. A. 1954. *Chemical Process Principles*. 2d ed. Wiley, New York, pp.v.

Hu, P., Bowen, S. H., Lewis, R. S. 2011. A Thermodynamic Analysis of Electron Production During Syngas Fermentation. Bioresource Technology, 102 (17), 8071-8076.

Ivey, D. M., Ljungdahl, L. G. 1986. Purification and Characterization of the Fl-Atpase from *Clostridium Thermoaceticum*. J. Bacteriol., 165 (1), 252-257.

Klasson, K. T., Ackerson, C. M. D., Clausen, E. C., Gaddy, J. L. 1992. Biological Conversion of Synthesis Gas into Fuels. International Journal of Hydrogen Energy, 17 (4), 281-288.

Kundiyana, D. K., Wilkins, M. R., Maddipati, P., Huhnke, R. L. 2011. Effect of Temperature, Ph and Buffer Presence on Ethanol Production from Synthesis Gas by "*Clostridium ragsdalei*". Bioresource Technology, 102 (10), 5794-5799.

Lehninger, A. L. 1982. *Principles of Biochemistry*. Worth Publishers, New York, N. Y, Liu, K., Atiyeh, H. K., Tanner, R. S., Wilkins, M. R., Huhnke, R. L. 2012. Fermentative Production of Ethanol from Syngas Using Novel Moderately Alkaliphilic Strains of Alkalibaculum Bacchi. Bioresource Technology, 104, 336-341.

Maddipati, P., Atiyeh, H. K., Belimer, D. D., Huhnke, R. L. 2011. Ethanol Production from Syngas by *Clostridium* Strain P11 Using Corn Steep Liquor as a Nutrient Replacement to Yeast Extract. Bioresource Technology, 102 (11), 6494-6501.

Medema, M. H., van Raaphorst, R., Takano, E., Breitling, R. 2012. Computational Tools for the Synthetic Design of Biochemical Pathways. Nature Reviews Microbiology, 10 (3), 191-202.

Munasinghe, P. C., Khanal, S. K. 2010. Syngas Fermentation to Biofuel: Evaluation of Carbon Monoxide Mass Transfer Coefficient (K(L)a) in Different Reactor Configurations. Biotechnology Progress, 26 (6), 1616-1621.

Nicholls, D. G., Ferguson, S. J. 2002. *Bioenergetics*. 3rd ed. Academic Press, pp. 297.

Phillips, J. R., Atiyeh, H. K., Lewis, R. S., Huhnke, R. L. 2011. Mass Transfer and Kinetic Limitations During Synthesis Gas Fermentation by Acetogenic Bacteria. *American Society of Agricultural and Biological Engineers Annual International Meeting* 2011, Aug. 7, 2011-Aug. 10, 2011, Louisville, Ky., United states. American Society of Agricultural and Biological Engineers. pp. 4567-4578.

Phillips, J. R., Clausen, E. C., Gaddy, J. L. 1994. Synthesis Gas as Substrate for the Biological Production of Fuels and Chemicals. Applied Biochemistry and Biotechnology, 45-6, 145-157.

Phillips, J. R., Klasson, K. T., Clausen, E. C., Gaddy, J. L. 1993. Biological Production of Ethanol from Coal Synthesis Gas—Medium Development Studies. Applied Biochemistry and Biotechnology, 39, 559-571.

Ragsdale, S. 2004. Life with Carbon Monoxide. Critical Reviews in Biochemistry & Molecular Biology, 39 (3), 165-195.

Ragsdale, S. W. 2008. Enzymology of the Wood-Ljungdahl Pathway of Acetogenesis. in: *Incredible Anaerobes: From Physiology to Genomics to Fuels*, (Eds.) J. Wiegel, R. J. Maier, M. W. W. Adams, Vol. 1125, pp. 129-136.

Ragsdale, S. W., Ljungdahl, L. G. 1984. Hydrogenase from Acetobacterium-Woodii. Archives of Microbiology, 139 (4), 361-365.

Ramachandriya, K. D., DeLorme, M. J., Wilkins, M. R. 2010. Heat Shocking of *Clostridium* Strain P11 to Promote Sporulation and Ethanol Production. Biological Engineering, 2 (2), 115-131.

Rogers, P., 1.-S Chen and M. J. Zidwick. 2006. Organic Acid and Solvent Production. in: *The Prokaryotes*, (Eds.) M.

Dworkin, S. Falkow, E. Rosenberg, K.-H. Schleifer, E. Stackebrandt, Springer New York, pp. 511-755.

Strobl, G., Feicht, R., White, H., Lottspeich, F., Simon, H. 1992. The Tungsten-Containing Aldehyde Oxidoreductase from *Clostridium-Thermoaceticum* and Its Complex with a Viologen-Accepting Nadph Oxidoreductase. Biological Chemistry Hoppe-Seyler, 373 (3), 123-132.

Thauer, R. K., Jungermann, K., Decker, K. 1977. Energy Conservation in Chemotrophic Anaerobic Bacteria. Microbiol. Mol. Biol. Rev., 41 (1), 100-180.

Tracy, B. P., Jones, S. W., Fast, A. G., Indurthi, D. C., Papoutsakis, E. T. 2012. Clostridia: The Importance of Their Exceptional Substrate and Metabolite Diversity for Biofuel and Biorefinery Applications. Current Opinion in Biotechnology, 23 (3), 364-381.

Vega, J. L., Antorrena, G. M., Clausen, E. C., Gaddy, J. L. 1989. Study of Gaseous Substrate Fermentations: Carbon Monoxide Conversion to Acetate. 2. Continuous Culture. Biotechnology and Bioengineering, 34 (6), 785-793.

von Ballmoos, C., Cook, G. M., Dimroth, P. 2008. Unique Rotary Atp Synthase and Its Biological Diversity. Annual Review of Biophysics, 37, 43-64.

White, H., Strobl, G., Feicht, R, Simon, H. 1989. Carboxylic-Acid Reductase—a New Tungsten Enzyme Catalyzes the Reduction of Non-Activated Carboxylic-Acids to Aldehydes. European Journal of Biochemistry, 184 (1), 89-96.

Thus, the present invention is well adapted to carry out the objects and attain the ends and advantages mentioned above as well as those inherent therein. While the inventive device has been described and illustrated herein by reference to certain preferred embodiments in relation to the drawings attached thereto, various changes and further modifications, apart from those shown or suggested herein, may be made therein by those of ordinary skill in the art, without departing from the spirit of the inventive concept the scope of which is to be determined by the following claims.

What is claimed is:

1. A method of operating a fermentation reactor comprising:
   (a) providing a fermentation reactor having a gas inlet, a gas outlet, and an energy input, wherein said energy input comprises
      agitating a liquid medium inside the fermentation reactor, or
      pumping the liquid medium inside the fermentation reactor;
   (b) providing the liquid medium inside the fermentation reactor;
   (c) providing an autotrophic acetogenic bacteria in the liquid medium;
   (d) providing syngas into the gas inlet at a flow rate;
   (e) obtaining an effluent gas at said gas outlet;
   (f) determining $p^*_{CO}$, where $p^*_{CO}$ is a partial pressure of dissolved carbon monoxide in the liquid medium;
   (g) controlling either the flow rate of syngas, the energy input or both to favor hydrogen uptake in said liquid medium over carbon dioxide and carbon monoxide based on said $p^*_{CO}$, wherein:
      (i) if said $p^*_{CO}$ is greater than $2\times10^{-3}$ kPa, then either decreasing the syngas flow rate or decreasing the energy input or both and
      (ii) if said $p^*_{CO}$ is less than $2\times10^{-3}$ kPa, then either increasing the syngas flow rate or increasing the energy input or both.

2. The method according to claim 1,
   wherein the step of controlling either the flow rate of syngas, the energy input or both to favor hydrogen uptake in said liquid medium over carbon dioxide and carbon monoxide based on said $p^*_{CO}$, comprises:
      if said $p^*_{CO}$ is greater than $2\times10^{-3}$ kPa, decreasing the syngas flow rate and
      if said $p^*_{CO}$ is less than $2\times10^{-3}$ kPa, increasing said syngas flow rate.

3. The method according to claim 1,
   wherein the step of controlling either the flow rate of syngas, the energy input or both to favor hydrogen uptake in said liquid medium over carbon dioxide and carbon monoxide based on said $p^*_{CO}$, comprises:
      if said $p^*_{CO}$ is greater than $2\times10^{-3}$ kPa, decreasing said energy input and
      if said $p^*_{CO}$ is less than $2\times10^{-3}$ kPa, increasing said energy input.

4. The method according to claim 3, wherein said energy input is agitating the liquid medium, and the liquid medium is agitated using a variable speed agitator operating at a first speed, and
   wherein the step of decreasing said energy input if said $p^*_{CO}$ is greater than $2\times10^{-3}$ kPa comprises decreasing said agitator first operating speed to a second operating speed less than said first operating speed if said $p^*_{CO}$ is greater than $2\times10^{-3}$ kPa, and
   wherein the step of increasing said energy input if said $p^*_{CO}$ is less than $2\times10^{-3}$ kPa comprises increasing said agitator first speed to a second speed greater than said first speed if said $p^*_{CO}$ is less than $2\times10^{-3}$ kPa.

5. The method according to claim 1, wherein the partial pressure of dissolved carbon monoxide is obtained by solving for said $p^*_{CO}$ using:

$$\frac{p^*_{CO2} p^*_{H2}}{p^*_{CO}} = e^{\left(\frac{-\Delta G_r^0}{RT}\right)} = 101.3 e^{\left(\frac{(19.93)}{(0.008314)(310.2)}\right)} = 230{,}100 \text{ kPa}$$

where,
   $p^*_{CO}$ is said partial pressure of dissolved carbon monoxide,
   $p^*_{H2}$ is a partial pressure of dissolved hydrogen,
   $p^*_{CO2}$ is a partial pressure of dissolved carbon dioxide,
   R is an ideal gas constant,
   T is a temperature, and
   $\Delta G_r^o$ is a Gibbs free energy change for the water gas shift reaction.

6. The method according to claim 5, wherein the partial pressure of dissolved hydrogen and the partial pressure of dissolved carbon dioxide are calculated by solving for $p^*_{H2}$ and $p^*_{CO2}$, where:

$$p^*_{H2} = \frac{\left(p_{H2,i} - p_{H2,o} \exp\left[\frac{\left(\frac{k_{L,H2}a}{V_L}\right)(p_{H2,i} - p_{H2,o})}{H_{H2}\left(-\frac{1}{V_L}\frac{dn_{H2}}{dt}\right)}\right]\right)}{\left(1 - \exp\left[\frac{\left(\frac{k_{L,H2}a}{V_L}\right)(p_{H2,i} - p_{H2,o})}{H_{H2}\left(-\frac{1}{V_L}\frac{dn_{H2}}{dt}\right)}\right]\right)}$$

and

-continued $$p^*_{CO2} = \frac{p_{CO2,i} - p_{CO2,o}\exp\left[\frac{\left(\frac{k_{L,CO2}a}{V_L}\right)}{H_{CO2}}\frac{(p_{CO2,i} - p_{CO2,o})}{\left(-\frac{1}{V_L}\frac{dn_{CO2}}{dt}\right)}\right]}{1 - \exp\left[\frac{\left(\frac{k_{L,CO2}a}{V_L}\right)}{H_{CO2}}\frac{(p_{CO2,i} - p_{CO2,o})}{\left(-\frac{1}{V_L}\frac{dn_{CO2}}{dt}\right)}\right]}$$

where
$p^*_{H2}$ is said partial pressure of dissolved hydrogen,
$p^*_{CO2}$ is said partial pressure of dissolved carbon dioxide,
$k_{L,H2}$ is a volumetric mass transfer coefficient for hydrogen,
$k_{L,CO2}$ is a volumetric mass transfer coefficient for carbon dioxide,
$H_{H2}$ is Henry's Law constant for hydrogen,
$H_{CO2}$ is Henry's Law constant for carbon dioxide,
a is an area of a gas liquid interface,
$V_L$ is a liquid volume into which the gas is transferred,
$p_{H2,i}$ is a partial pressure of $H_2$ in said syngas,
$p_{H2,o}$ is a partial pressure of $H_2$ in said effluent gas,
$p_{CO2,i}$ is a partial pressure of carbon dioxide in said syngas,
$p_{CO2,o}$ is a partial pressure of carbon dioxide in said effluent gas,
$dn_{H2}/dt$ is a molar transfer rate of hydrogen, and
$dn_{CO2}/dt$ is a molar transfer rate of carbon dioxide.

7. The method of claim 6, wherein the volumetric mass transfer coefficient for carbon dioxide is obtained by solving for $k_{L,CO2}$ in:

$$\left(\frac{k_{L,CO}a}{V_L}\right) = \sqrt{\frac{D_{CO,W}}{D_{CO2,W}}}\left(\frac{k_{L,CO2}a}{V_L}\right)$$

where,
$k_{L,CO2}$ is said volumetric mass transfer coefficient for carbon dioxide,
$k_{L,CO}$ is a volumetric mass transfer coefficient for carbon monoxide,
a is an area of a gas-liquid interface,
$V_L$ is a liquid volume into which gas is transferred,
$D_{CO,W}$ is a diffusivity of carbon monoxide in water, and
$D_{CO2,W}$ is a diffusivity of carbon dioxide in water.

8. The method of claim 7, wherein the volumetric mass transfer coefficient for hydrogen is calculated by solving for $k_{L,H2}$ in:

$$\left(\frac{k_{L,CO}a}{V_L}\right) = \sqrt{\frac{D_{CO,W}}{D_{H2,W}}}\left(\frac{k_{L,H2}a}{V_L}\right)$$

where,
$k_{L,H2}$ is said volumetric mass transfer coefficient for hydrogen,
$k_{L,CO}$ is said volumetric mass transfer coefficient for carbon monoxide,
a is an area of a gas-liquid interface,
$V_L$ is a liquid volume into which gas is transferred,
$D_{CO,W}$ is a diffusivity of carbon monoxide in water, and
$D_{H2,W}$ is a diffusivity of hydrogen in water.

9. The method of claim 8, wherein the volumetric mass transfer coefficient for carbon monoxide is calculated by solving for $k_{L,CO}$ in:

$$\left(\frac{k_{L,CO}a}{V_L}\right) = \frac{H_{CO}}{V_L}\frac{dn_{CO}}{dt}\frac{\ln\left(\frac{p_{CO,i}}{p_{CO,o}}\right)}{p_{CO,i} - p_{CO,o}}$$

where,
$k_{L,CO}$ is said volumetric mass transfer coefficient for carbon monoxide,
$V_L$ is a liquid volume into which the carbon monoxide is transferred,
a is an area of a gas liquid interface,
$H_{CO}$ is a Henry's Law constant for carbon monoxide,
$p_{CO,i}$ is a partial pressure of carbon monoxide in said syngas,
$p_{CO,o}$ is a partial pressure of carbon monoxide in said effluent gas, and
$dn_{CO}/dt$ is a molar rate of transfer of carbon monoxide.

10. The method of claim 1, wherein the autotrophic acetogenic bacteria is *Clostridium ragsdalei* or *Clostridium ljungdahlii*.

11. A method of operating a fermentation reactor comprising:
(a) providing a fermentation reactor having a gas inlet, a gas outlet, and an energy input, wherein said energy input comprises
agitating a liquid medium inside the fermentation reactor, or
pumping the liquid medium inside the fermentation reactor;
(b) providing the liquid medium inside the fermentation reactor;
(c) providing an autotrophic acetogenic bacteria in the liquid medium;
(d) providing syngas into the gas inlet at a flow rate;
(e) obtaining an effluent gas at said gas outlet;
(f) determining $p^*_{CO}$, where $p^*_{CO}$ is a partial pressure of dissolved carbon monoxide in the liquid medium; and
(g) controlling either the flow rate of syngas, the energy input or both to favor hydrogen uptake in said liquid medium over carbon dioxide and carbon monoxide based on said $p^*_{CO}$, wherein:
(i) if said $p^*_{CO}$ is greater than $2\times10^{-4}$ kPa, then either decreasing the syngas flow rate or decreasing the energy input or both and
(ii) if said $p^*_{CO}$ is less than $2\times10^{-4}$ kPa, then either increasing the syngas flow rate or increasing the energy input or both.

12. The method according to claim 11,
wherein the step of controlling either the flow rate of syngas, the energy input or both to favor hydrogen uptake in said liquid medium over carbon dioxide and carbon monoxide based on said $p^*_{CO}$, comprises:
if said $p^*_{CO}$ is greater than $2\times10^{-4}$ kPa decreasing the syngas flow rate and
if said $p^*_{CO}$ is less than $2\times10^{-4}$ kPa, increasing said syngas flow rate.

13. The method according to claim 11,
wherein the step of controlling either the flow rate of syngas, the energy input or both to favor hydrogen uptake in said liquid medium over carbon dioxide and carbon monoxide based on said $p^*_{CO}$, comprises:

if said $p^*_{CO}$ is greater than $2\times10^{-4}$ kPa, decreasing said energy input and if said $p^*_{CO}$ is less than $2\times10^{-4}$ kPa, increasing said energy input.

14. The method of claim 13, wherein the autotrophic acetogenic bacteria is *Clostridium ragsdalei* or *Clostridium ljungdahlii*.

* * * * *